(12) United States Patent
King

(10) Patent No.: US 9,026,228 B2
(45) Date of Patent: May 5, 2015

(54) TRANSVERSE TRIPOLE NEUROSTIMULATION LEAD, SYSTEM AND METHOD

(75) Inventor: Gary W. King, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 2717 days.

(21) Appl. No.: 11/380,886

(22) Filed: Apr. 28, 2006

(65) Prior Publication Data

US 2006/0253182 A1    Nov. 9, 2006

Related U.S. Application Data

(63) Continuation-in-part of application No. 11/256,220, filed on Oct. 21, 2005.

(60) Provisional application No. 60/728,854, filed on Oct. 21, 2005, provisional application No. 60/621,007, filed on Oct. 21, 2004.

(51) Int. Cl.
 *A61N 1/00*   (2006.01)
 *A61N 1/05*   (2006.01)

(52) U.S. Cl.
 CPC ............ *A61N 1/0551* (2013.01); *A61N 1/0553* (2013.01)

(58) Field of Classification Search
 USPC .......................................... 607/46, 115–118
 See application file for complete search history.

(56) References Cited

U.S. PATENT DOCUMENTS

| | | | |
|---|---|---|---|
| 5,417,719 A * | 5/1995 | Hull et al. | 607/46 |
| 5,501,703 A * | 3/1996 | Holsheimer et al. | 607/46 |
| 5,643,330 A | 7/1997 | Holsheimer | |
| 5,895,416 A | 4/1999 | Barreras | |
| 6,236,892 B1 * | 5/2001 | Feler | 607/117 |
| 2004/0260310 A1 | 12/2004 | Harris | |

* cited by examiner

*Primary Examiner* — Christopher D Koharski
*Assistant Examiner* — Roland Dinga

(57) ABSTRACT

An implantable neurostimulation lead, method and system adapted for tripolar electric simulation and/or field steering. The neurostimulation lead is are adapted to provide an electrode array defining, for example, a plurality of electrode sets that may be used to provide tripolar stimulation and/or electric field steering.

10 Claims, 26 Drawing Sheets

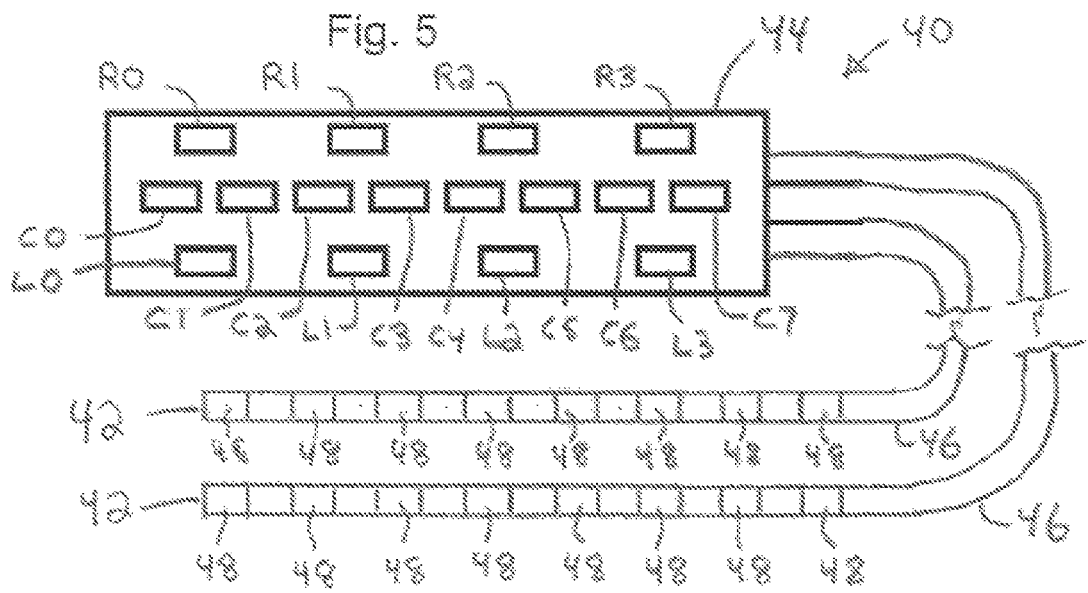
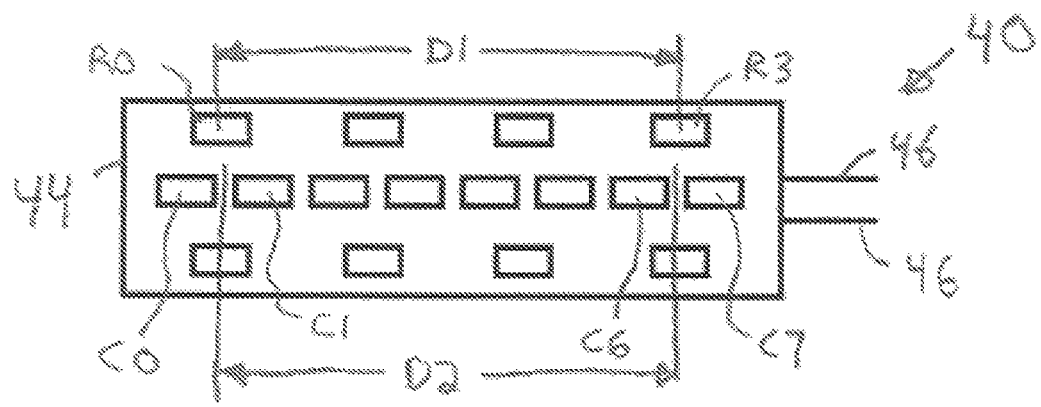

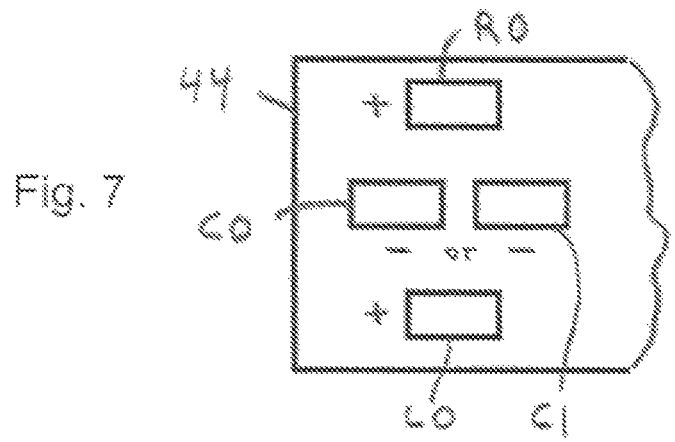
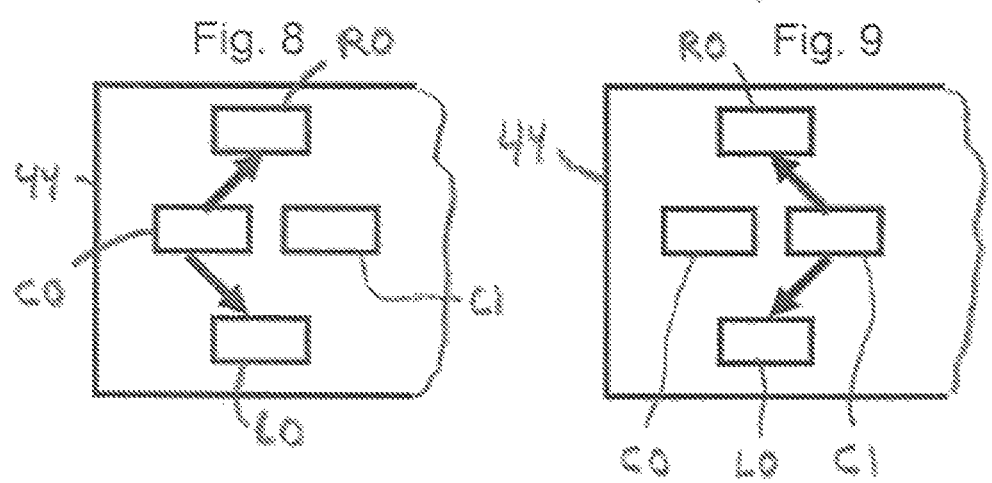
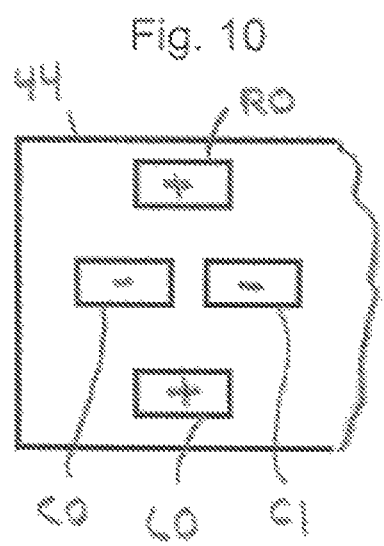
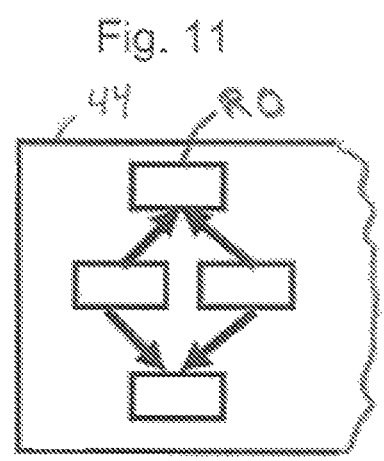

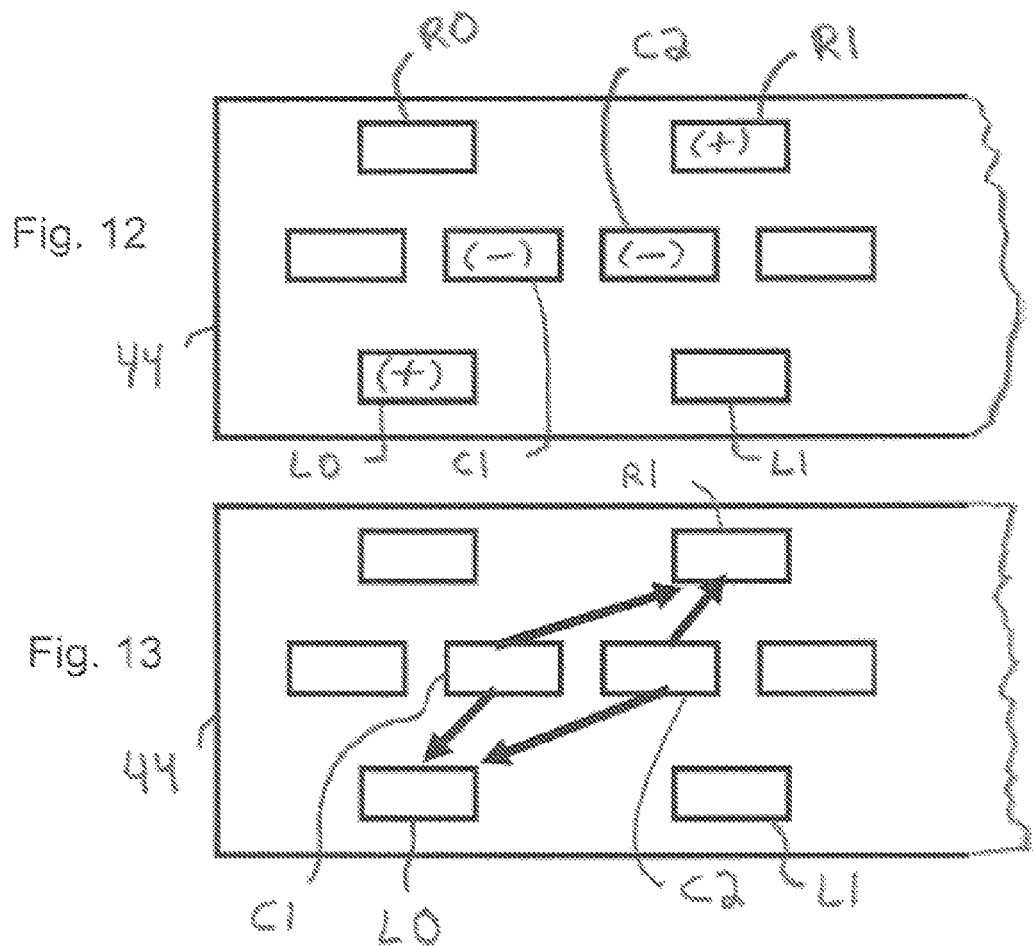
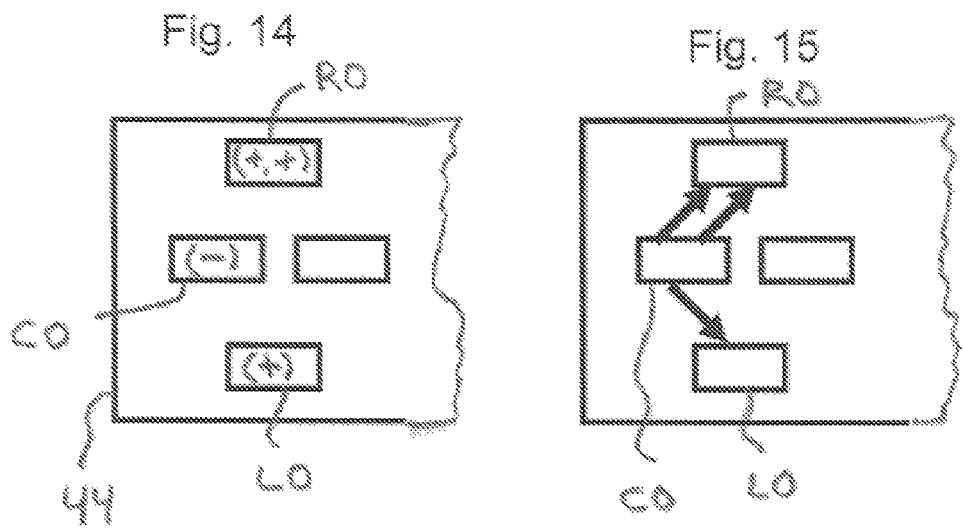

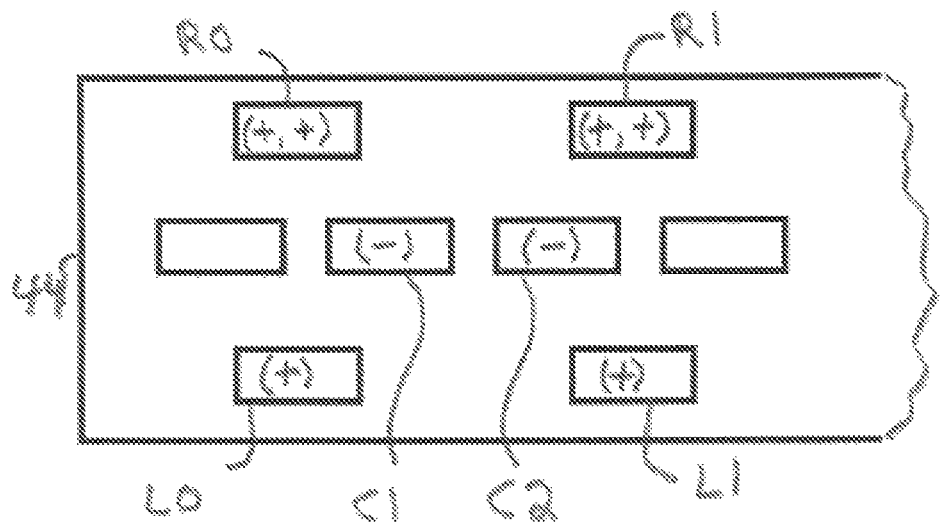
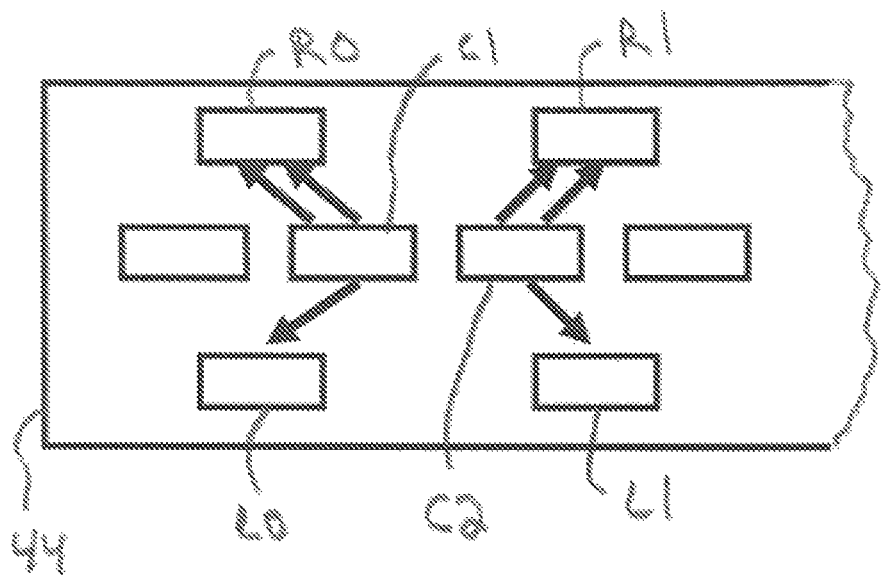

Fig. 18
Table A - Voltage Controlled Stimulation

| | L0 | L1 | L2 | L3 | C0 | C1 | C2 | C3 | C4 | C5 | C6 | C7 | R0 | R1 | R2 | R3 |
|---|---|---|---|---|---|---|---|---|---|---|---|---|---|---|---|---|
| Electrode configuration of figure 7 | 4V | | | | 0V | | | | | | | | 4V | | | |
| Electrode configuration of figure 10 | 4V | | | | 0V | 0V | | | | | | | 4V | | | |
| Electrode configuration of figure 14 | 2V | | | | 0V | | | | | | | | 5V | | | |
| Electrode configuration of figure 12 | 4V | | | | | 0V | 0V | | | | | | | 4V | | |
| Electrode configuration of figure 16 | 2V | 2V | | | | 0V | 0V | | | | | | 5V | 5V | | |

Fig. 19
Table B – Voltage Controlled Stimulation

| | L0 | L1 | L2 | L3 | C0 | C1 | C2 | C3 | C4 | C5 | C6 | C7 | R0 | R1 | R2 | R3 |
|---|---|---|---|---|---|---|---|---|---|---|---|---|---|---|---|---|
| Electrode configuration of figure 7 | 2V | | | | -2V | | | | | | | | 2V | | | |
| Electrode configuration of figure 10 | 2V | | | | -2V | -2V | | | | | | | 2V | | | |
| Electrode configuration of figure 14 | 1V | | | | -1V | | | | | | | | 2.5V | | | |
| Electrode configuration of figure 12 | 2V | | | | | -2V | -2V | | | | | | | 2V | | |
| Electrode configuration of figure 16 | 1V | 1V | | | | -1V | -1V | | | | | | 2.5V | 2.5V | | |

Fig 20
Table C – Current Controlled Stimulation

| | L0 | L1 | L2 | L3 | C0 | C1 | C2 | C3 | C4 | C5 | C6 | C7 | R0 | R1 | R2 | R3 |
|---|---|---|---|---|---|---|---|---|---|---|---|---|---|---|---|---|
| Electrode configuration of figure 8 | +5ma | | | | -10ma | | | | | | | | +5ma | | | |
| Electrode configuration of figure 11 | +5ma | | | | -5ma | -5ma | | | | | | | +5ma | | | |
| Electrode configuration of figure 15 | +3ma | | | | -10ma | | | | | | | | +7ma | | | |
| Electrode configuration of figure 13 | +5ma | | | | | -5ma | -5ma | | | | | | | +5ma | | |
| Electrode configuration of figure 17 | +3ma | +3ma | | | | -5ma | -5ma | | | | | | +7ma | +7ma | | |

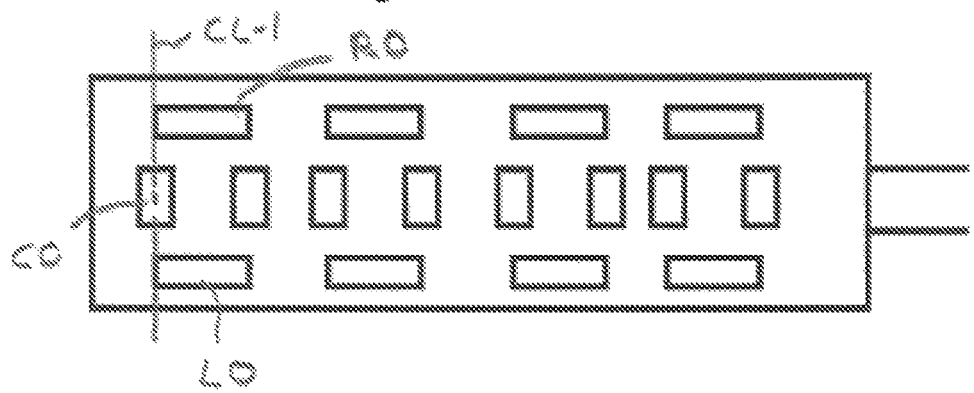
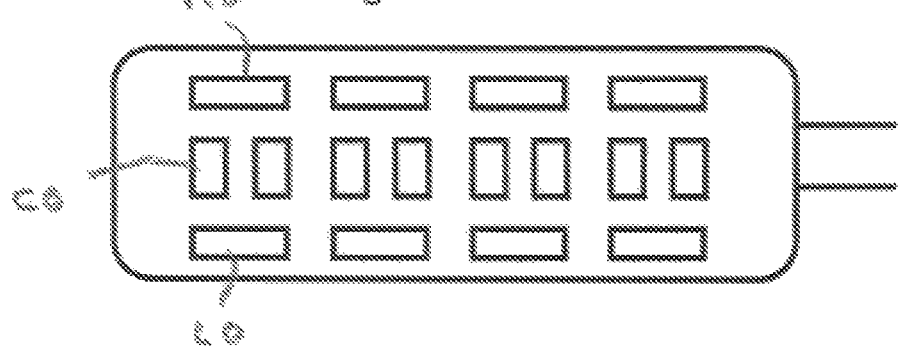
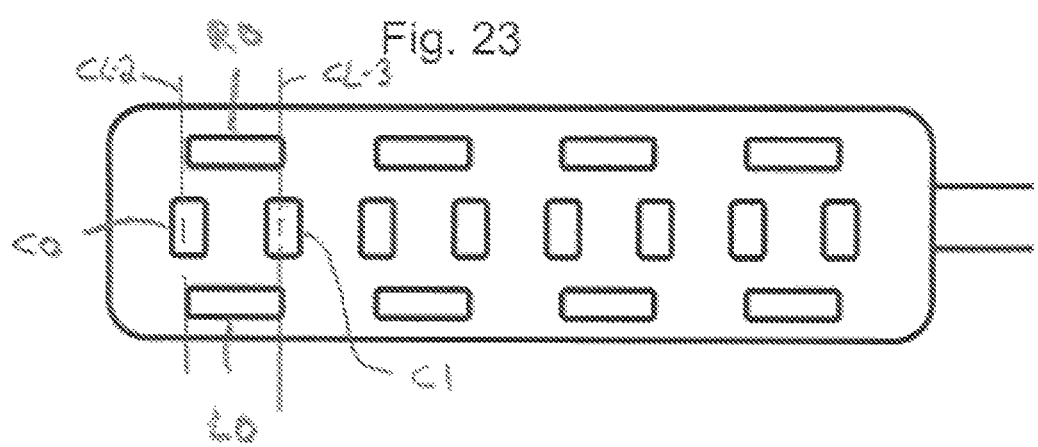

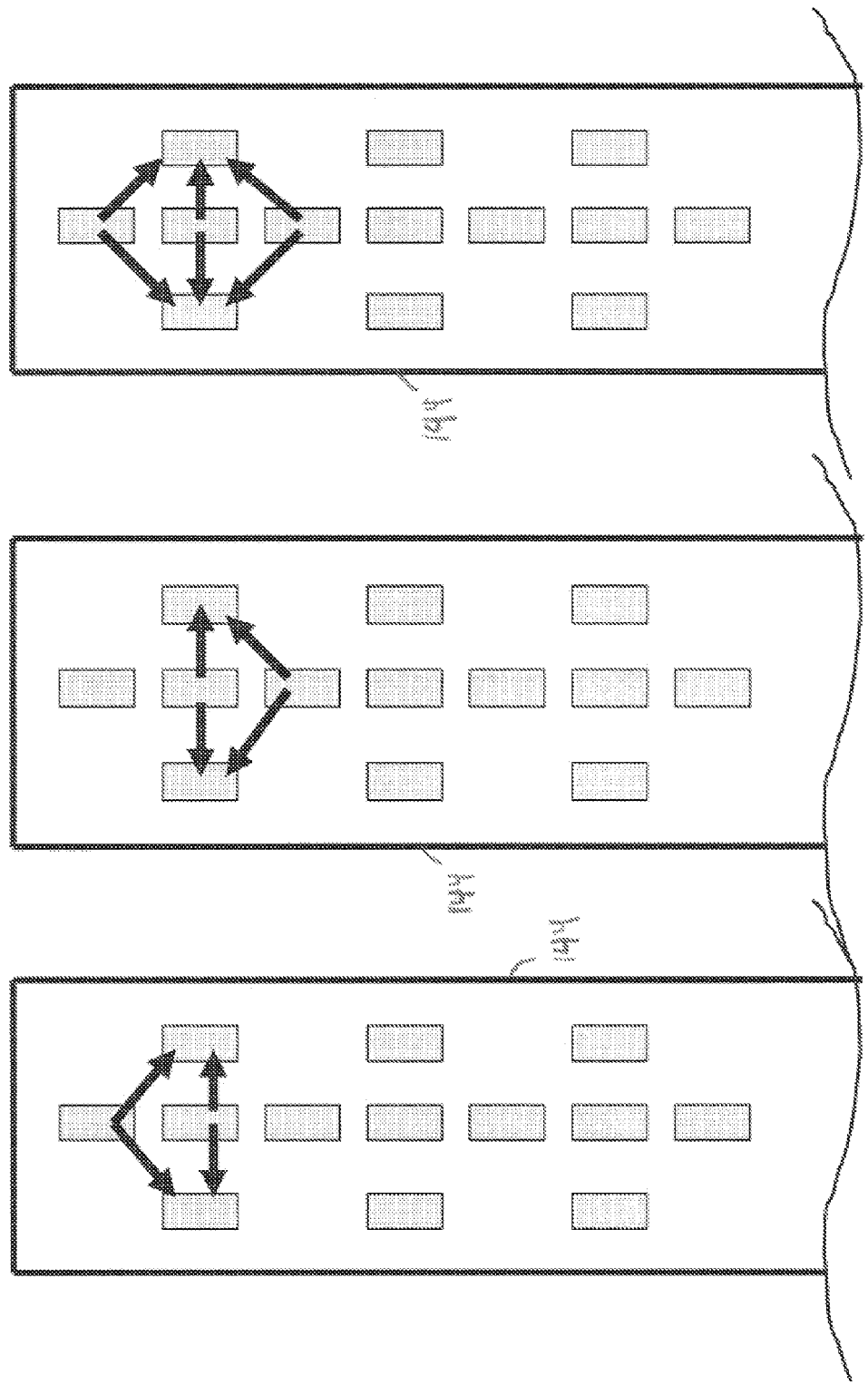

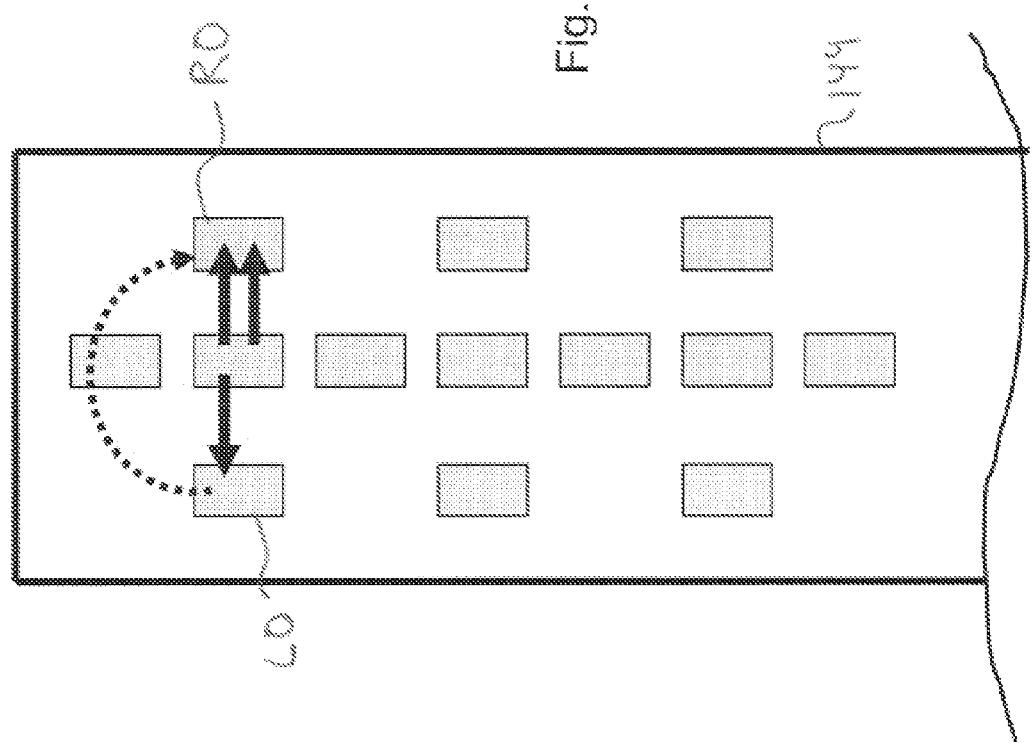

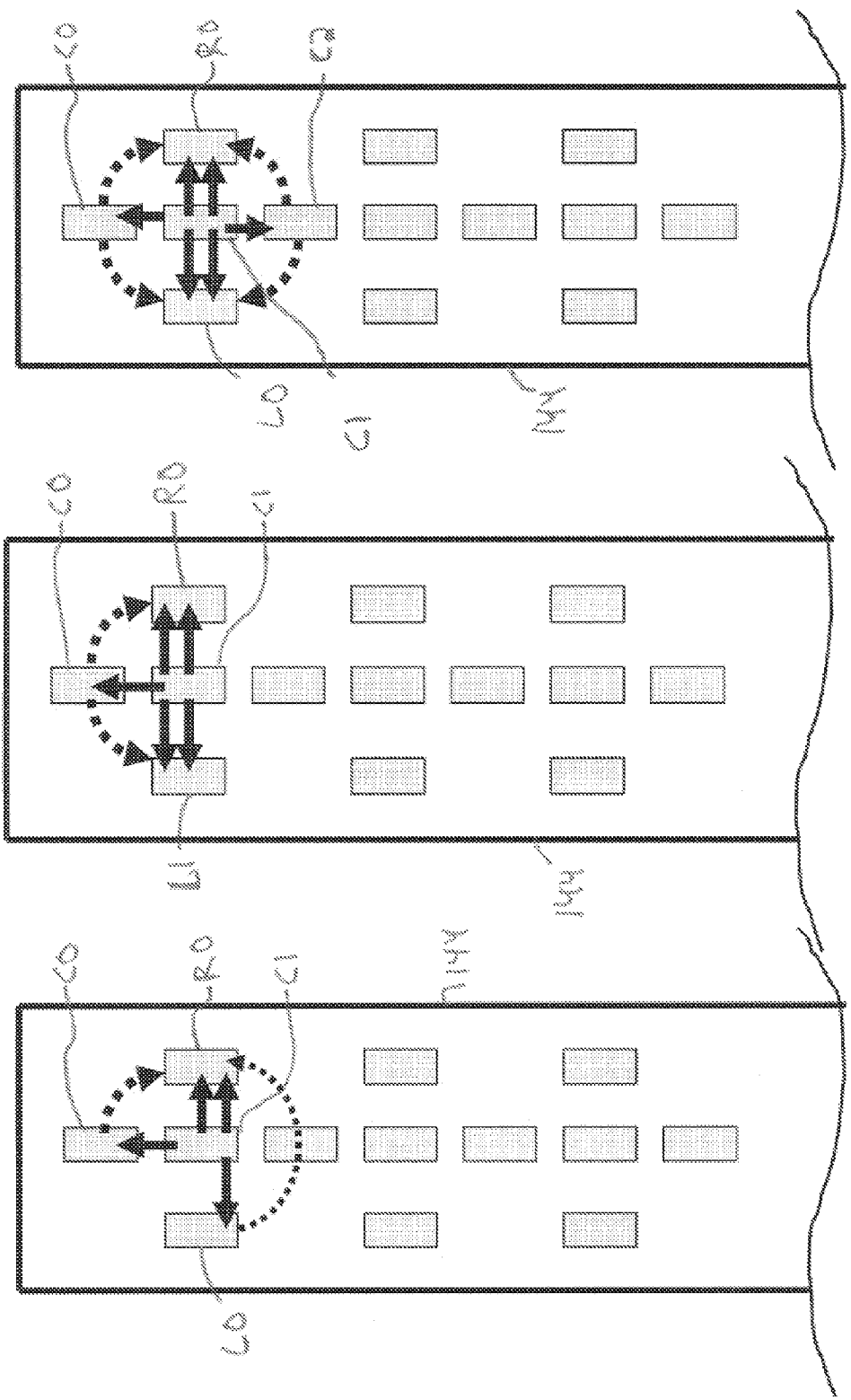

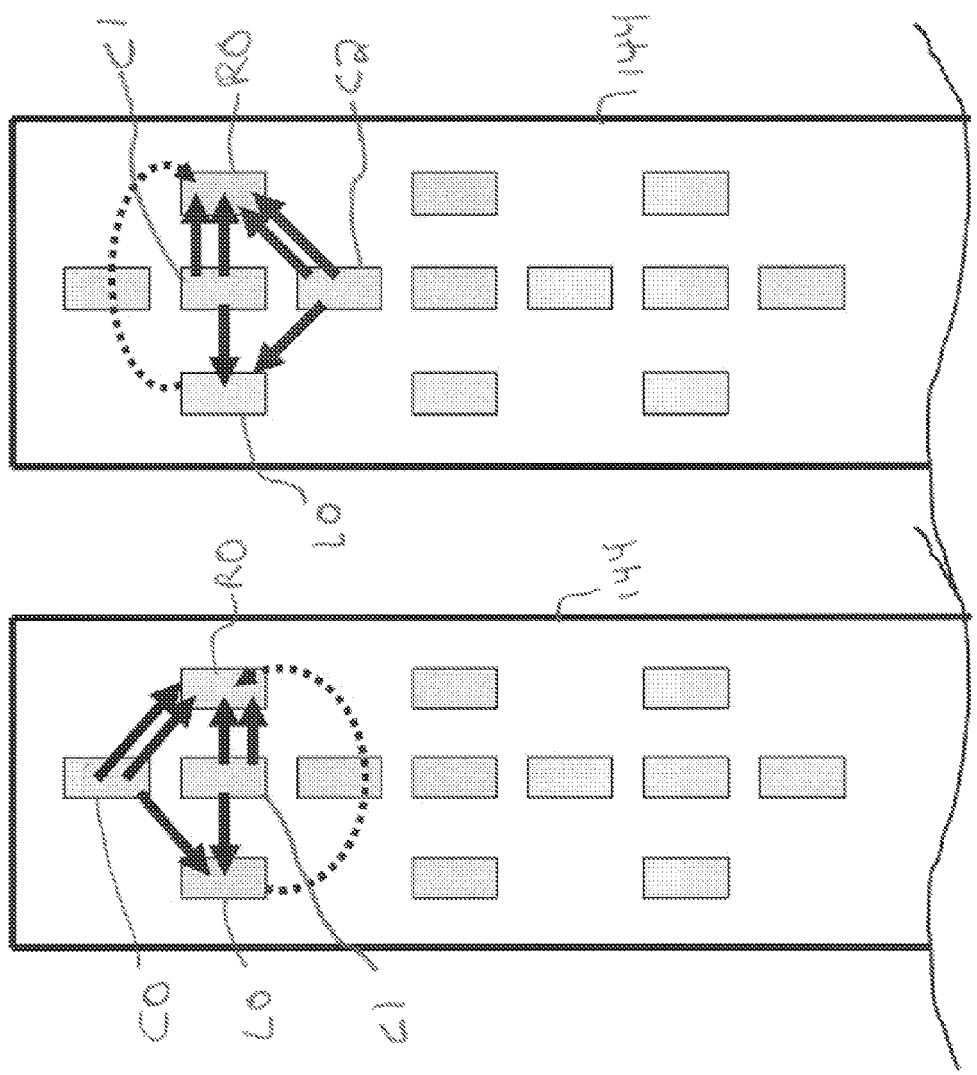

Figure 48
Table D - Voltage Controlled Stimulation

| Electrode Configuration of Figure | L0 | L1 | C0 | C1 | C2 | C3 | C4 | C5 | R0 | R1 |
|---|---|---|---|---|---|---|---|---|---|---|
| 28 | 4V |  | 0V |  |  |  |  |  | 4V |  |
| 29 | 4V |  |  | 0V |  |  |  |  | 4V |  |
| 30 | 4V |  |  |  | 0V |  |  |  | 4V |  |
| 31 | 4V |  | 0V | 0V |  |  |  |  | 4V |  |
| 32 | 4V |  |  | 0V | 0V |  |  |  | 4V |  |
| 33 | 4V |  | 0V | 0V | 0V |  |  |  | 4V |  |
| 34 | 4V |  |  | 0V | 4V |  |  |  | 4V |  |
| 35 | 4V |  | 4V | 0V | 4V |  |  |  | 4V |  |
| 36 | 4V |  |  | 4V | 0V |  |  |  | 4V |  |
| 37 | 4V | 4V |  | 4V | 0V | 4V |  |  | 4V | 4V |
| 38 |  | 4V |  |  | 0V | 0V |  |  | 4V |  |
| 39 |  | 4V |  |  | 0V | 0V |  |  | 4V |  |
| 40 |  | 4V |  |  |  |  | 0V |  | 4V |  |
| 41 |  | 4V |  |  | 0V |  | 0V |  | 4V |  |
| 42 | 2V |  |  | 0V |  |  |  |  | 5V |  |
| 43 | 2V |  | 2V | 0V |  |  |  |  | 5V |  |
| 44 | 5V |  | 2V | 0V | 2V |  |  |  | 5V |  |
| 45 | 5V |  | 3V | 0V | 3V |  |  |  | 5V |  |
| 46 | 2V |  |  | 0V | 0V |  |  |  | 5V |  |
| 47 | 2V |  |  |  | 0V | 0V |  |  | 5V |  |

Figure 49
Table E - Voltage Controlled Stimulation

| Electrode Configuration of Figure | L0 | L1 | C0 | C1 | C2 | C3 | C4 | C5 | R0 | R1 |
|---|---|---|---|---|---|---|---|---|---|---|
| 28 | 2V | | -2V | | | | | | 2V | |
| 29 | 2V | | | -2V | | | | | 2V | |
| 30 | 2V | | | | -2V | | | | 2V | |
| 31 | 2V | | -2V | -2V | | | | | 2V | |
| 32 | 2V | | | -2V | -2V | | | | 2V | |
| 33 | 2V | | -2V | -2V | -2V | | | | 2V | |
| 34 | 2V | | | -2V | 2V | | | | 2V | |
| 35 | 2V | | 2V | 2V | | | | | 2V | |
| 36 | 2V | | | 2V | -2V | | | | 2V | |
| 37 | 2V | 2V | | | -2V | 2V | | | 2V | 2V |
| 38 | | 2V | | | -2V | | | | 2V | |
| 39 | | 2V | | | -2V | -2V | | | 2V | |
| 40 | | 2V | | | | -2V | -2V | | 2V | |
| 41 | | 2V | | | -2V | | -2V | | 2V | |
| 42 | 2V | | 2V | -2V | | | | | 5V | |
| 43 | 2V | | 2V | -2V | 2V | | | | 5V | |
| 44 | 5V | | 2V | -2V | 3V | | | | 5V | |
| 45 | 5V | | 3V | -3V | | | | | 5V | |
| 46 | 2V | | | -2V | -2V | | | | 5V | |
| 47 | 2V | | | | -2V | -2V | | | 5V | |

Figure 50
Table F - Current Controlled Stimulation

| Electrode Configuration of Figure | L0 | L1 | C0 | C1 | C2 | C3 | C4 | C5 | R0 | R1 |
|---|---|---|---|---|---|---|---|---|---|---|
| 28 | +5mA | | -10mA | | | | | | | |
| 29 | +5mA | | | -10mA | | | | | +5mA | |
| 30 | +5mA | | | | -10mA | | | | +5mA | |
| 31 | +5mA | | -5mA | -5mA | | | | | +5mA | |
| 32 | +5mA | | | -5mA | -5mA | | | | +5mA | |
| 33 | +5mA | | -3.3mA | -3.3mA | -3.3mA | | | | +5mA | |
| 34 | +5mA | | | -15mA | +5mA | | | | +5mA | |
| 35 | +5mA | | +5mA | -20mA | +5mA | | | | +5mA | |
| 36 | +5mA | | | +5mA | -15mA | | | | +5mA | |
| 37 | +5mA | +5mA | | +5mA | -30mA | +5mA | | | +5mA | +5mA |
| 38 | | +5mA | | | -10mA | | | | +5mA | |
| 39 | | +5mA | | | -5mA | -5mA | | | +5mA | |
| 40 | | +5mA | | | | -5mA | -5mA | | +5mA | |
| 41 | | +5mA | | | -3.3mA | -3.3mA | -3.3mA | | +5mA | |
| 42 | +3mA | | +3mA | -10mA | | | | | +7mA | |
| 43 | +3mA | | +2mA | -13mA | | | | | +7mA | |
| 44 | +5mA | | +3mA | -12mA | | | | | +5mA | |
| 45 | +7mA | | +3mA | -20mA | | | | | +7mA | |
| 46 | +2mA | | | | +3mA | | | | +5mA | |
| 47 | +2mA | | -3.5mA | -3.5mA | -3.5mA | -3.5mA | | | +5mA | |

TRANSVERSE TRIPOLE NEUROSTIMULATION LEAD, SYSTEM AND METHOD

RELATED APPLICATIONS

This application claims priority to provisional U.S. Application No. 60/728,854, filed Oct. 21, 2005, and is a continuation-in-part of U.S. patent application Ser. No. 11/256,220, filed Oct. 21, 2005, which claims priority to provisional U.S. Application No. 60/621,007, filed Oct. 21, 2004. The foregoing applications are incorporated herein by reference in their entireties.

FIELD

This application relates to electrical stimulation of biological tissue, and more particularly to methods and systems for neurostimulation, for example, of the spinal cord with a tripole orientated generally transverse to the axis of the spinal cord.

BACKGROUND

Transverse tripole stimulation ("TTS") may involve, for example, at least three electrodes arranged substantially along a line approximately perpendicular to the axis of the spinal cord. The electrical field can be steered from side to side by varying the current or voltage between the center electrode and the outer electrodes. Voltages or currents can be in phase (overlapping in time) or out of phase between the right and left side. Using the outer electrodes as anodes may prevent nerve root stimulation.

See, e.g., U.S. Pat. Nos. 5,501,703; 5,643,330 and 5,895,416.

BRIEF SUMMARY

As used herein, the term, "exemplary" is used in the sense of "for example" or "for purposes of illustration," and not in a limiting sense.

In a first exemplary embodiment, an implantable electrode array, which is adapted for epidural implantation for electrically stimulating the spinal cord, generally comprises first, second and third longitudinally extending columns with each column including a plurality of stimulation electrodes spaced apart. The first and second columns are laterally spaced apart from the third column along opposite sides of the third column. The stimulation electrodes of the first and second columns have substantially similar center-to-center spacing of adjacent electrodes, and the stimulation electrodes of the third column have a center-to-center spacing of adjacent electrodes that is no greater than approximately one half of the center-to-center spacing of adjacent electrodes of the first and second columns.

In a second exemplary embodiment, an implantable electrode array generally comprises first, second and third longitudinally extending columns with each column including a plurality of stimulation electrodes spaced apart. The first and second columns are laterally spaced apart from the third column along opposite sides of the third column. The stimulation electrodes of the first and second columns have substantially similar center-to-center spacing of adjacent electrodes, and the ratio of the number of stimulation electrodes of the third column relative to the number of electrodes of either the first or second columns is at least approximately two.

In a third exemplary embodiment, an implantable neurostimulation lead generally comprises a lead body and a paddle mounted on the lead body and defining a longitudinal direction. The paddle has an electrode array comprising first, second and third longitudinally extending columns with each column including a plurality of stimulation electrodes spaced apart along the paddle. The first and second columns are laterally spaced apart from the third column along opposite sides of the third column. The stimulation electrodes of the first and second columns have substantially similar center-to-center spacing of adjacent electrodes, and the stimulation electrodes of the third column have a center-to-center spacing of adjacent electrodes that is approximately one half of the center-to-center spacing of adjacent electrodes of the first and second columns.

In a fourth exemplary embodiment, an implantable neurostimulation lead generally comprises a lead body, and a paddle mounted on the lead body and defining a longitudinal direction. The paddle has an electrode array comprising first, second and third longitudinally extending columns with each column including a plurality of stimulation electrodes spaced apart. The first and second columns are laterally spaced apart from the third column along opposite sides of the third column. The stimulation electrodes of the first and second columns have substantially similar center-to-center spacing of adjacent electrodes, and the ratio of the number of stimulation electrodes of the third column relative to the number of electrodes of either the first or second columns is at least approximately two.

In a fifth exemplary embodiment, an implantable neurostimulation lead for epidural spinal cord stimulation generally comprises a lead body and a paddle mounted on the lead body and defining a longitudinal direction and a transverse direction. The paddle has an electrode array comprising first, second and third columns wherein the first and second columns are laterally spaced apart from the third column along opposite sides of the third column. Each of the first and second columns has a plurality of stimulation electrodes longitudinally spaced apart along the paddle wherein the plurality of stimulation electrodes of the first and second columns define a plurality of transverse pairs of stimulation electrodes. One stimulation electrode of each transverse pair is located on the first column and the other stimulation electrode of each transverse pair is located on the second column. Each transverse pair of stimulation electrodes is so located along the first and second columns that the transverse pair of stimulation electrodes is adapted to define a transverse line generally transverse relative to the spinal cord after implantation of the lead. The third column has a plurality of longitudinal pairs of adjacent stimulation electrodes corresponding to the transverse pairs of transverse stimulation electrodes of the first and second columns wherein each such longitudinal pair of adjacent stimulation electrodes forms an electrode set with one of the transverse pairs of stimulation electrodes. A distal stimulation electrode of such longitudinal pair is positioned along the third column such that the distal stimulation electrode is displaced distally of the transverse line defined by the transverse pair of stimulation electrodes of that electrode set, and a proximal stimulation electrode of such longitudinal pair is positioned along the third column such that the proximal stimulation electrode is adapted to be displaced proximally of the transverse line defined by the transverse pair of stimulation electrodes of that electrode set.

In a sixth exemplary embodiment, a method of electrically stimulating the spinal cord with the electric stimulation lead generally comprises implanting the lead in the epidural space of a patient, and programming the stimulation electrodes to create a tripole in which at least one electrode is active on each of the first, second and third column within at least one of the electrode sets.

BRIEF DESCRIPTION OF THE DRAWINGS

FIG. 5 shows an embodiment of the paddle portion of the neurostimulation lead used in the neurostimulation system of FIGS. 1 and 2.

FIG. 6 shows the exemplary embodiment of FIG. 5 illustrating the relative spacing between electrodes in each column relative to the other columns.

FIG. 7 illustrates an exemplary embodiment in which a moderately longitudinally skewed active electrodes selected in the paddle portion of FIGS. 5 and 6.

FIG. 8 illustrates the exemplary embodiment of FIGS. 6 and 7 with arrows indicating direction of electron flow, which, while applicable to both voltage controlled and current controlled devices, is particularly shown to illustrate current controlled embodiments.

FIG. 9 is similar to FIG. 8 with an alternative selection of a central electrode.

FIG. 10 illustrates an embodiment in which the lead of FIGS. 7 and 8 have non-skewed active electrodes selected generally perpendicular to the axis of the spinal cord (also perpendicular to the axes of the leads) with two center electrodes selected.

FIG. 11 illustrates the exemplary embodiment of claim 9 with arrows indicating direction of electron flow, which, while applicable to both voltage controlled and current controlled devices, is particularly shown to illustrate current controlled embodiments.

FIG. 12 illustrates an embodiment in which the exemplary lead of FIGS. 7-11 have skewed active electrodes selected with a greater degree of skewing than FIG. 7-9.

FIG. 13 illustrates the exemplary embodiment of FIG. 12 with arrows indicating direction of electron flow, which, while applicable to both voltage controlled and current controlled devices, is particularly shown to illustrate current controlled embodiments.

FIG. 14 illustrates an embodiment in which the lead of FIGS. 7-13 have active electrodes selected and provided with pulses of different voltage amplitudes (e.g., the right outer electrode has a greater amplitude voltage pulse than the left outer electrode), illustrating independent control and electric field steering using a voltage controlled scheme.

FIG. 15 is similar to FIG. 14 except that different amplitude current pulses are provided to the outer electrodes, illustrating independent control and field steering using a current controlled scheme.

FIG. 16 illustrates an embodiment in which the lead of FIGS. 7-15 have additional electrodes selected in a non-skewed active array to form a wider field than in the embodiments of FIGS. 7-15 and in which different amplitude voltage pulses are provided to the outer electrodes to steer the electric field generated by the electrodes.

FIG. 17 is similar to FIG. 16 except that different amplitude current pulses are provided to the outer electrodes, illustrating independent control and field steering using a current controlled scheme.

FIGS. 18-20 show Tables A, B and C, which illustrate various exemplary electrode program configurations with either voltage or current controlled electrical waveforms, and each table includes an illustrative cross reference to the figures.

FIGS. 21-26 are front plan views of various alternative embodiments of the paddle portion of exemplary paddle-type leads.

FIG. 27 is a front plan view with a portion broken away illustrating an exemplary embodiment of a paddle-type lead in which alternate center electrodes are aligned with opposite side electrodes.

FIGS. 28-47 are top plan views similar to FIG. 27 illustrating various stimulation programs involving selective controlled activation of electrodes to form various tripole stimulation configurations.

FIGS. 48-50 show Tables D, E and F, which illustrate various exemplary electrode program configurations with either voltage or current controlled electrical waveforms, and each table includes an illustrative cross reference to the figures.

DETAILED DESCRIPTION OF EXEMPLARY EMBODIMENTS

Figure 1:
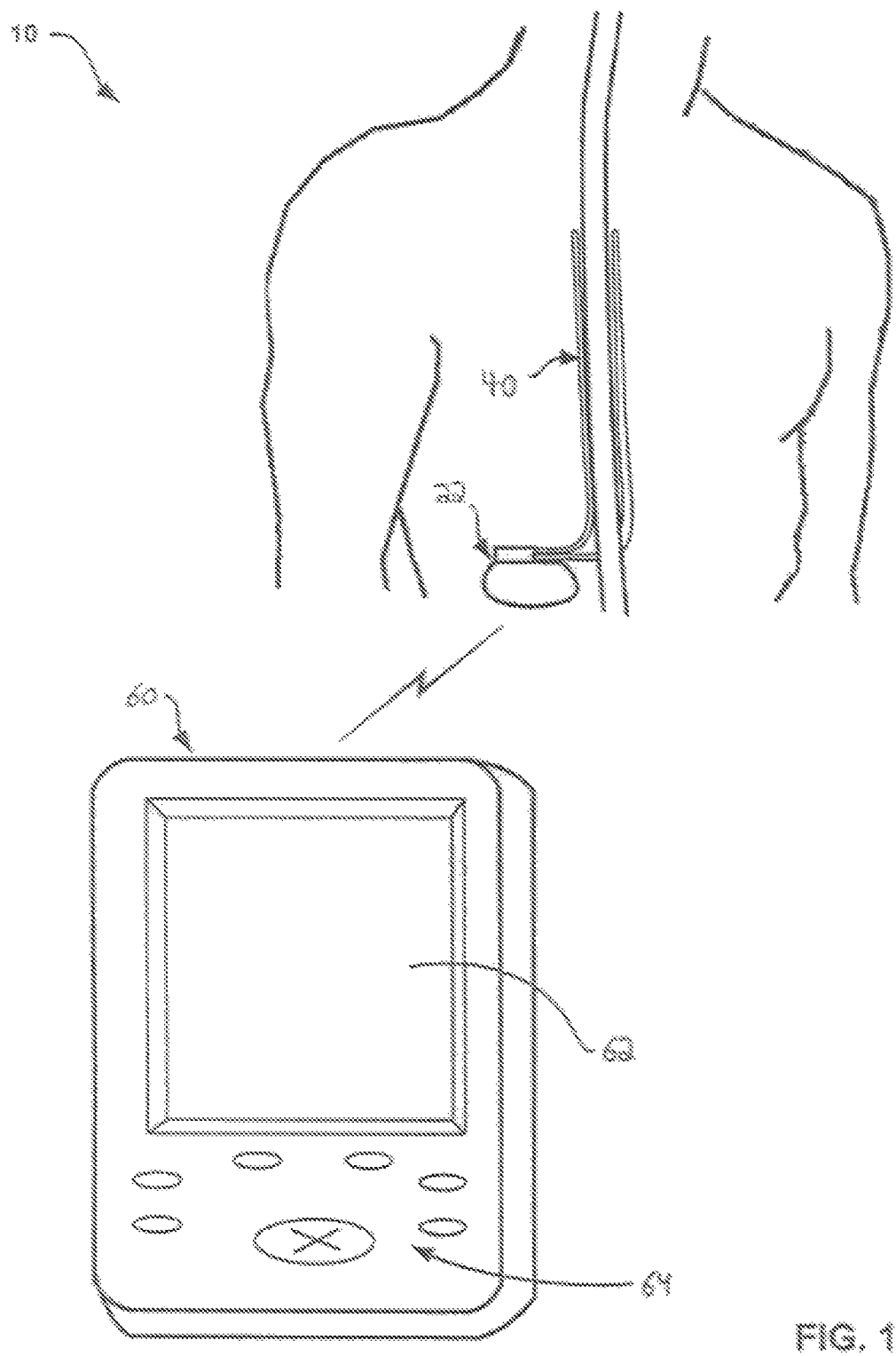
FIG. 1 shows a general environmental view for an embodiment of a neurostimulation system used to stimulate the spinal cord.
Figure 2:
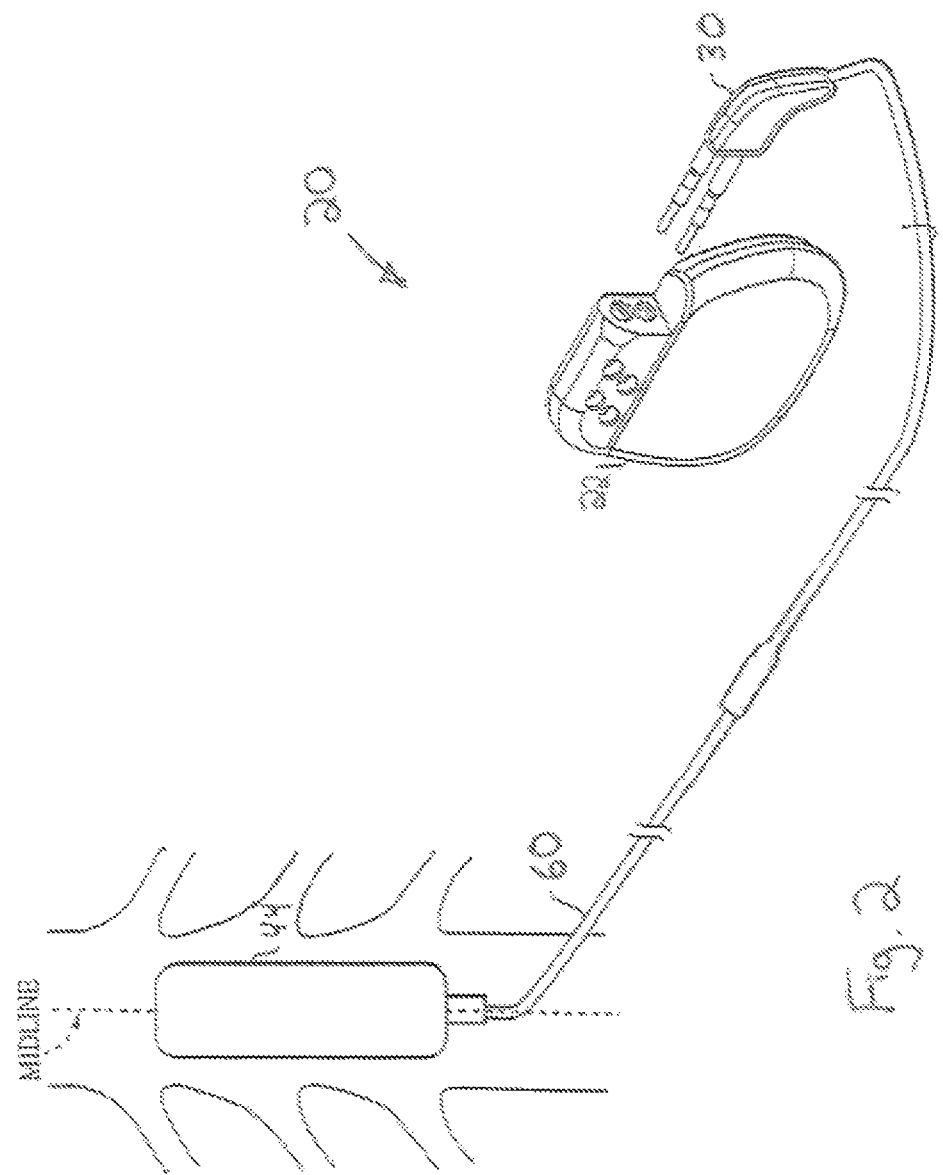
FIG. 2 shows the neurostimulation system of FIG. 1 with the paddle of a paddle style lead arranged in the epidural space.

FIG. 1 shows a general environmental view 10 for an exemplary implantable neurostimulation system embodiment. Neurostimulation systems may be used to treat conditions such as pain, movement disorders, pelvic floor disorders, gastroparesis, and a wide variety of other medical conditions. As illustrated in FIGS. 1 and 2, the neurostimulation system 20 may include a neurostimulator 22 (e.g., implantable pulse or signal generator), one or more stimulation lead extension(s) 30, and one or more stimulation lead(s) 40. The neurostimulator 22 is typically implanted subcutaneously in the patient's body 28 at a location selected by the clinician. The stimulation lead 40 is typically fixed in place near the location selected by the clinician using a device such as an adjustable anchor.

Exemplary embodiments of such neurostimulator 22 may include a rechargeable or non-rechargeable battery or other power source, a processor, and a connector header for connection of a lead or lead extension to the IPG, as well as a telemetry antenna to allow communication with the IPG to or from an external device. The implantable pulse generator 22 is capable of generating multiple independent pulses occurring either simultaneously or one pulse shifting in time with respect to the other, and having independently varying amplitudes and pulse widths. While neurostimulator 22 typically provides electrical stimulation by way of pulses, other forms of stimulation may be used as continuous electrical stimulation. The term "pulse generator" as used herein is intended to cover generators that are capable of producing discrete pulses, as well as one that produce continuous electrical stimulation.

This exemplary system may employ a programmer 60. The programmer 60 permits attending medical personnel to select the various pulse output options after implant using radio frequency communications. While the exemplary system employs fully implanted elements, systems employing partially implanted generators and radio-frequency coupling may also practice the present invention. The system may also include a patient programmer (similar at the schematic level to the programmer 60) allowing the patient to select or modify the stimulation therapy program.

The neurostimulator 22 delivers neurostimulation therapy to patient according to one or more neurostimulation therapy programs. A neurostimulation therapy program may include values for a number of parameters, and the parameter values define a parameter configuration for delivery of the neurostimulation therapy delivered according to that program. In embodiments where neurostimulator 22 delivers neurostimulation therapy in the form of electrical pulses, the parameters may include pulse voltage or current amplitudes, pulse widths, pulse rates, durations and the like. Further, the lead 40 includes electrodes (not shown in FIG. 1), and the parameters for a program may include information identifying which electrodes have been selected for delivery of pulses according to the program, and the polarities of the selected electrodes. Hence, a parameter configuration may involve one or more of a variety of parameters including electrode configuration, amplitude, pulse width, pulse rate, and duration.

A selected subset of the electrodes located on lead 40 and the polarities of the electrodes of the subset collectively define an "electrode configuration." The electrodes may be arranged in a an array on a surgical paddle lead as described below. The electrodes may be associated with different target regions within a body of a patient. Electrode configurations refer to combinations of single or multiple cathode electrodes and single or multiple anode electrodes. Stimulation current flows between the cathodes and anodes for delivery of neurostimulation therapy. Hence, the polarities of the individual electrodes are another feature of the electrode configuration. Electrodes forming part of an electrode configuration may reside together on a single lead or on different leads System 10 may also includes a programmer 60. Programmer 60 may, as shown in FIG. 1, be a handheld computing device. Programmer 60 includes a display 62, such as a LCD or LED display, to display information to a user. Programmer 60 may also include a keypad 24, which may be used by a user to interact with programmer 60. In some embodiments, display 62 may be a touch screen display, and a user may interact with programmer 60 via display 62. A user may also interact with programmer 60 using peripheral pointing devices, such as a stylus or mouse. Keypad 64 may take the form of an alphanumeric keypad or a reduced set of keys associated with particular functions.

A clinician (not shown) may use programmer 60 to program neurostimulation therapy for patient. In particular, the clinician may use programmer 60 to create neurostimulation therapy programs. As part of the program creation process, programmer 60 allows the clinician to identify parameter configurations that enable neurostimulator 22 to deliver neurostimulation therapy that is desirable in terms of, for example, symptom relief, coverage area relative to symptom area, and side effects. Programmer 60 may also allow the clinician to identify parameter configurations that enable neurostimulator 22 to deliver effective neurostimulation therapy with desirable device performance characteristics, e.g., low battery consumption. In addition, techniques as described herein may used to optimize therapy over the course of use of a chronically implanted neurostimulator, e.g., by interaction between patient and a patient programmer to record efficacy observations over time.

While the preferred exemplary system employs fully implanted elements, systems employing partially implanted generators and radio-frequency coupling may also be used (e.g., similar to products sold by Medtronic, Inc. under the trademarks X-trel and Mattrix).

Figure 3:
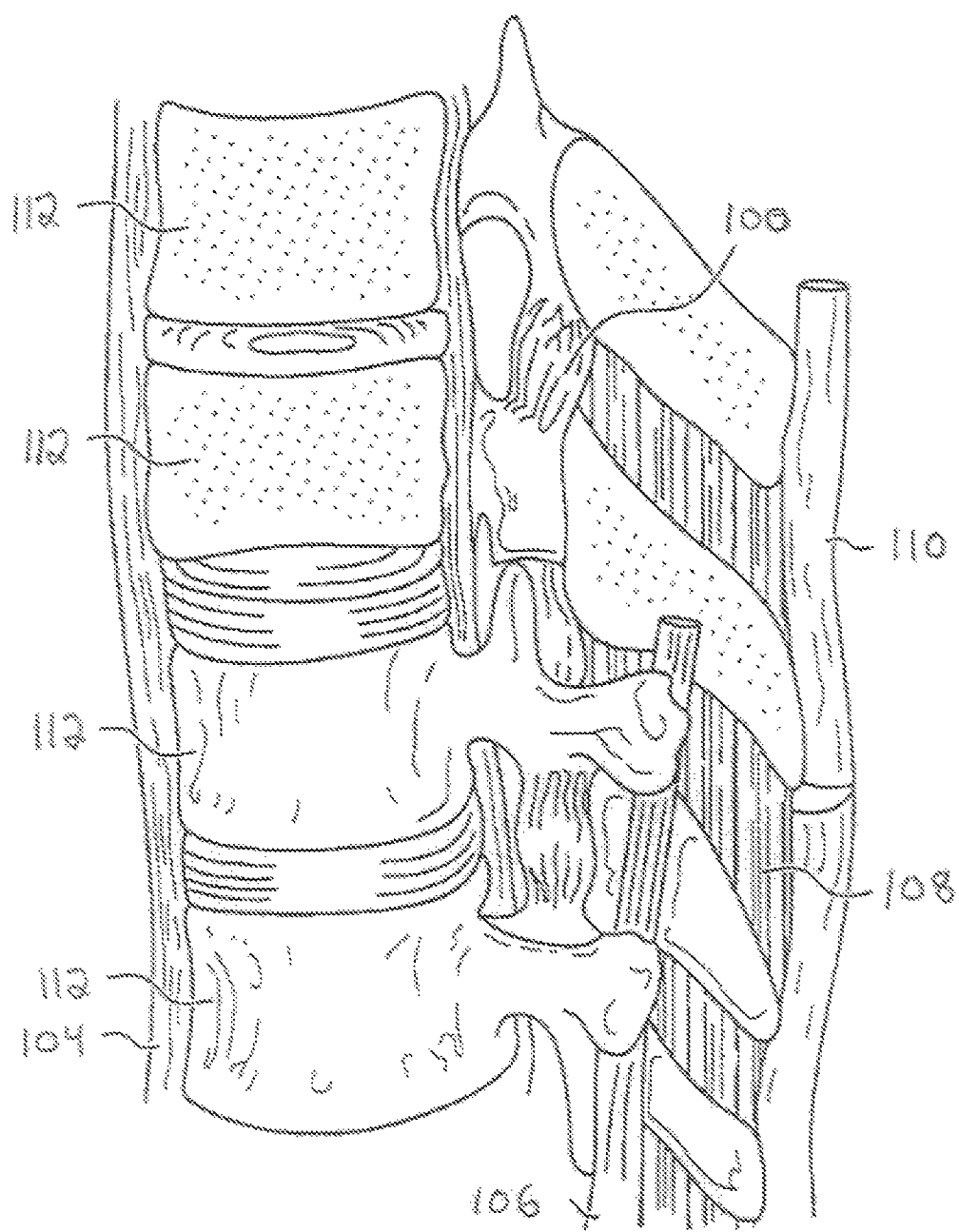
FIG. 3 illustrates various anatomical features of a portion of the vertebral column, including connective tissue, such as the ligamentum flavum through which medical leads are passed into the epidural space for electrical stimulation or sensing of the nerves of the spinal cord.
Figure 4:
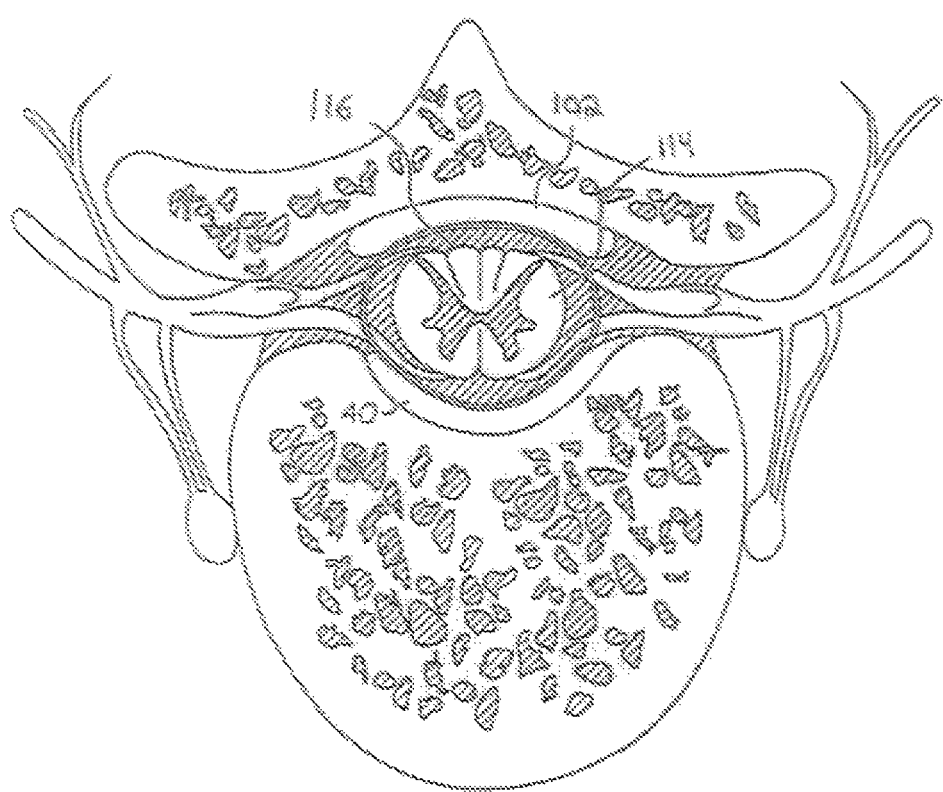
FIG. 4 is a cross sectional view along a transverse plane of a vertrebral column.
Figure 24:
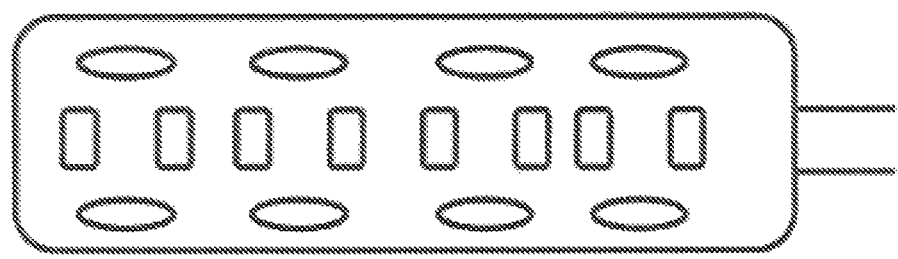
Figure 25:
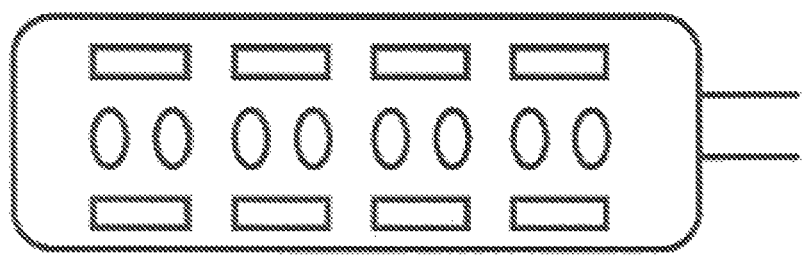
Figure 26:
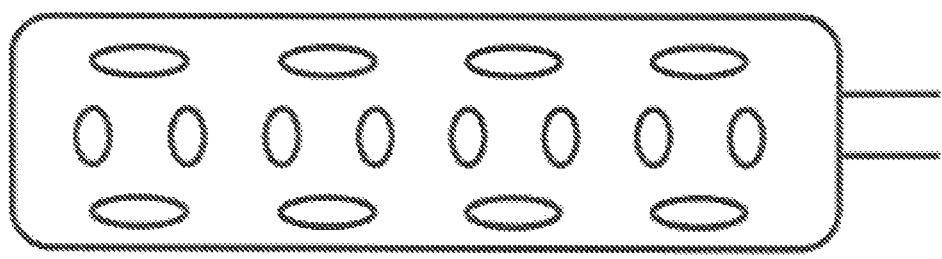

FIGS. 3 and 4 illustrate details of spinal or vertebral anatomy, including connective tissue, such as the ligamentum flavum 100 (FIG. 3) and the posterior epidural space 102 (FIG. 4). Exemplary embodiments of the medical lead 40 are adapted to be implanted through the ligamentum flavum 100 into the epidural space 102 into position for electrical spinal cord stimulation. FIG. 3 also illustrates, among other things, the anterior longitudinal ligament 104, intertransverse ligament 106, interspinal ligament 108, and supraspinal ligament 110, and, of course, vertebra 112. FIG. 4 also illustrates, among other things, the spinal cord 114, intrethecal space 116, and anterior epidural space 118.

The exemplary implantable neurostimulator 22 has a housing, a power supply in the housing 24, and stimulation electronics in the housing in electrical communication with the battery and in electrical communication with a connector block 26, which is also known as a terminal block.

The implantable neurostimulator 22 may be configured to provide current controlled pulses, voltage controlled pulses or both. The pulses are preferably independently variable (e.g., programmable) so that the voltage or current of each active electrode can be independently controlled. In current controlled embodiments (see, e.g., table C in FIG. 20), it is contemplated that each electrode could be an independently controllable current source or independently controllable current sink. An alternative embodiment of a current controlled-type neurostimulator 22 may include one or more electrodes that are programmed to be a voltage reference with other electrodes programmed to be current sources or current sinks. Tables A and B (FIGS. 18 and 19) illustrate some exemplary programs in which the electrodes are programmed in a voltage controlled scheme.

The exemplary stimulation lead 40 has a proximal end portion 42, a distal end portion 44 and at least one lead body 46 (preferably two lead bodies for example) extending between the proximal end portion 42 and distal end portion 44. The proximal end portion 42 has at least one electrical connector 48 (also known as electrical terminals or contacts), with various standard pluralities, such as four or eight electrical contacts, being typical. The distal end portion 44 has a generally paddle like configuration and has a plurality of stimulation electrodes (e.g., sixteen electrodes R0-R3, C0-C7 and L0-L3). As used herein, "paddle," "paddle-like" and "paddle-style" refer to a structure that is enlarged in at least one but typically opposite lateral directions of the lead as distinct from generally cylindrical structures. Exemplary paddles may be without limitation flat or substantially flat, curved or substantially curved, hinged or combinations of the foregoing (e.g., generally flat along one side and curved along the other).

When used in the context of a lead, the term "longitudinal" refers to the direction of elongation of the lead or paddle portion of the lead. "Lateral" or "transverse," when used in the context of a lead, refers to the direction generally perpendicular to the longitudinal direction of the lead or substantially parallel leads. When used in the context of the spinal cord, "longitudinal," "lateral" and "medial" are used in their common medically accepted meanings, e.g., "longitudinal" refers to the axial direction of the spinal cord. The term "transverse" when used in the context of a lead or electrode array relative to the spinal cord includes both the lateral direction relative to the spinal cord and diagonal directions relative to the spinal cord but in either case the term "transverse" implies some crossing over a center line or point defined with respect to the spinal cord or a central lead. All such terms are intended to have approximate practical meanings in view of the limp structure of exemplary preferred leads and the environment of use, rather than precise geometrical meanings.

In the context of a lead, "distal" means the longitudinal direction along the lead toward the free end of the lead (e.g., typically the end with tissue stimulating electrodes), and "proximal" refers to the longitudinal direction toward the end of the lead that is intended to be connected to an implantable neurostimulator 22, or a lead extension that is intended to connect the lead with such an neurostimulator 22. Because some exemplary leads may be typically somewhat flexible and limp such that the distal and proximal ends of the leads in a mechanical sense could be brought together, it will be understood that proximal and distal refer to relative positions along the length of the lead rather than a coordinate grid in absolute space.

There is at least one lead conductor 50 contained in the lead body 46 that is electrically connecting the electrical connector 48 to the stimulation electrodes 42. Typically, at least one conductor may be used to establish electrical communication between a single electrical connector/electrode pair, although alternative examples include multiplexing or bus features within the lead to allow use of fewer conductors along the length of the lead than the number of electrodes. As used herein, "conductive means" or "means for electrical communication between electrodes and electrical connectors" include the foregoing examples or any alternative structure that allows selection or electrical activation of one or more electrode.

Examples of suitable electrodes include generally rectangular, generally plate-like electrodes of the type illustrated in the FIGS. 7-17, as well as round, oval, rectangular with rounded corners or other suitable shapes. In one example, the electrodes have a surface area of approximately 6 mm$^2$, and in another example the electrodes have a generally oval shape with a surface area of approximately 12 mm$^2$ (3 mm×4 mm). FIGS. 21-26 illustrate various exemplary embodiment of electrode arrays showing various shaped electrodes and arrangements of electrodes within the array.

FIGS. 21-26 illustrate alternative embodiments of the paddle showing left outer and right outer electrodes that are longer and thinner than the center electrodes (which are thus relatively short and wide). For example, the outer electrodes may have a length of approximately 6 mm and a width of approximately 1 mm and the electrodes of the inner column may have a length of 4.5 mm and a width of 1.5 mm with the length of the center electrodes of this example being oriented generally or substantially in alignment lateral dimension of the paddle and the length of the electrodes of the outer columns being oriented generally or substantially in the longitudinal direction of the paddle.

Each of the center electrodes (e.g., C0) of the embodiment illustrated in FIG. 21 have a centerline (e.g., CL-1) in alignment with the ends of the adjacent side electrodes (e.g., R0, L0). Each of the center electrodes (e.g., C0) of the embodiment illustrated in FIG. 22 have a distal or proximal edge in alignment with the distal or proximal end of the adjacent side electrodes (e.g., R0, L0). In the embodiment illustrated in FIG. 23, the center electrodes (C0-C7) are equally spaced apart within the central column; the side electrodes (R0-R3 or L0-L3) are equally spaced apart within the side columns; and each of the center electrodes (e.g., C0, C1) have a centerline (e.g., CL-2, or CL-3) in alignment with the ends of the adjacent side electrodes (R0, L0). The centerlines CL-1, CL-2 and C1-3 of the embodiments illustrated in FIGS. 21 and 23 extend substantially in the lateral direction of the lead and are thus adapted to extend substantially in the transverse direction relative to the spinal cord.

The paddle itself may have a generally rectangular, rectangular with rounded corners, oval or other suitable configuration for the environment in which it is intended to be used. For example, the paddle would likely be generally elongate for placement in the epidural space with a suitable width, thickness and length for such placement.

As used herein, "transverse tripole stimulation" or "TTS" refers to any arrangement in which at least three electrodes are arranged with a substantial transverse component relative to the neural tissue being stimulated (e.g., along a line that substantially departs from the longitudinal axis of the spine). Examples include without limitation (a) at least three co-linear, epidural electrodes arranged along one or more lead(s) in a line approximately perpendicular to the spinal cord axis, (b) at least three co-linear, epidural electrodes in a line skewed with respect to (i.e. substantially not parallel with) the longitudinal axis of the spinal cord to provide a substantial transverse component to the electrical field generated by the electrodes, and (c) at least three non co-linear, epidural electrodes that provide a substantial transverse component to the electrical field generated by the electrodes, as well as other arrangements in which at least three electrodes are arranged with a substantial transverse component relative to the neural tissue being stimulated.

"Outer" in the context of electrodes forming a tripole set refers to the outer electrodes forming the outer part of a tripole array where the "center" or "medial" electrode(s) form(s) the inner part of the tripole array. In the context of a transverse tripole, the spacing of the outer electrodes from the inner electrode(s) will include a lateral component, where lateral is defined relative to the spinal cord. The outer electrodes may also be referred to as either right or left electrodes.

Electrodes may also be identified by the following conventions: L0, L1, . . . , LN; C0, C1, . . . , CN; R0, R1, . . . , RN; where "L" refers to an electrode on the left outer column, "C" refers to an electrode on the center column, and "R" refers to an electrode on the right outer column. The associated numbering (e.g., L0 to LN) refers to an order starting at the distal end of the lead, with "N" refers to the number of electrodes in the column minus 1. An alternative convention is to number the electrodes from E0 to EN, where "N" refers to the total number of electrodes connected to the neurostimulator 22 minus 1 (e.g., N=15 if the neurostimulator is designed to work with 16 electrodes). Other conventions may also be employed, and the described convention are merely provided as exemplary illustrations.

In TTS, the electrical field can be steered from side to side by varying the current or voltage between the electrodes. Examples include without limitation varying the current or voltage of the two outer electrodes independently of each other, or independently varying the current or voltage between the center electrode(s) and outer electrodes. Voltages or currents may be in phase (overlapping in time) or out of phase between the right and left side.

A first exemplary embodiment of transverse tripole stimulation ("TTS") may employ a paddle-style lead having an electrode array arranged in three columns: two four-electrode columns and one eight-electrode column. Each four-electrode column may have four electrodes that may be arranged in line along the longitudinal direction of the paddle, and the eight-electrode column may have eight electrodes that may be arranged in line along the longitudinal direction of the paddle. This exemplary embodiment is illustrated in FIG. 4, with four electrodes L0, L1, L2 and L3 in the right column; eight electrodes C0, C1, C2, C3, C4, C5, C6 and C7 in the central column; and four electrodes R0, R1, R2 and R3 in the right column. A second exemplary embodiment may include electrodes distributed as follows: five electrodes on the right and left columns, and six electrodes on the center column. It will be understood that the number of electrodes in each column and the total number of electrodes could be varied from these exemplary embodiment.

Most preferably, the lead in this exemplary embodiment is what is typically referred to as a surgical or paddle-type lead.

In the first exemplary embodiment (e.g., FIGS. 5-17), the relative spacing of electrodes in each of the three columns is selected such that the electrodes of the three columns match up in a symmetric way. This may be accomplished, for example, by having the distance $D_1$ between the centers of the outboard electrodes on the four-electrode leads equal to the distance $D_2$ between the centers of the outboard spaces on the eight-electrode lead, as shown in the FIG. 5. As used herein, "spaces" refers to the spaces between adjacent electrodes in a column, and "outboard" refers to the longitudinal extremes, e.g., the distal most electrode (e.g., L0, C0, or R0), the proximal most electrode (e.g., LN, CN, or RN), the space between the distal most electrode and its adjacent electrode, or the space between the proximal most electrode and its adjacent electrode.

In the first exemplary embodiment, the electrode lengths and spaces may be consistent on each column, although it may be preferred for the electrode lengths and spacing not to be equal between the four-electrode columns and the eight-electrode column. For example, the four-electrode column may have 3 mm length electrodes and 6 mm spaces between adjacent electrodes, whereas the eight-electrode column may have 3.5 mm length electrodes and 1 mm spaces between adjacent electrodes. The term "adjacent" as used with respect to electrodes on the same column does not refer to proximity per se (because adjacent electrodes may be separated by meaningful distances) but merely refers to the absence of intermediate electrodes between the adjacent electrodes.

Exemplary equations for determining an exemplary preferred relationship between columns in a 4-8-4 electrode lead embodiment include the following:

$S_E$=space between adjacent electrodes in column
$L_E$=length of electrode in lead
$D_1=3\times S_E+3\times L_E$ (four-electrode columns)
$D_2=6\times S_E+6\times L_E$ (eight-electrode column)
$D_1=D_2$ For example, one exemplary preferred embodiment may include two four-electrode columns with 3 mm length electrodes and 6 mm spacing between electrodes, and one eight-electrode column with 3 mm length electrodes and 1.5 mm spacing between adjacent electrodes:

For $D_1$: $L_E$=3 mm; $S_E$=6 mm
For $D_2$: $L_E$=3 mm; $S_E$=1.5 mm
$D_1=3\times 6+3\times 3=27$
$D_2=6\times 1.5+6\times 3=27$
$D_1=D_2$ Alternatively, a second exemplary preferred embodiment may include a four-electrode column with 3 mm length electrodes and 4 mm spacing between adjacent electrodes, and an eight electrode column with 2.5 mm length electrodes and 1.0 mm spacing between electrodes:

For $D_1$: $L_E$=3 mm; $S_E$=4 mm
For $D_2$: $L_E$=2.5 mm; $S_E$=10 mm
$D_1=3\times 4+3\times 3=21$
$D_2=6\times 1+6\times 2.5=21$
$D_1=D_2$ An alternative exemplary equation involves employing outer columns having twice the center-to-center spacing between adjacent electrodes than employed in the center column. As used in this context with a paddle-style lead having plate electrodes, the "center" of an electrode means the centerline of the electrode that is approximately perpendicular to the longitudinal axis of the lead. For example, if the electrode length $L_E$=3 mm and the spacing between electrodes $S_E$=4 mm for an outer or side lead, the center-to-center spacing would be 7 mm. In that case a preferred exemplary embodiment of the center column would include electrodes having a length $L_E$=2.5 mm and spacing between electrodes $S_E$=1.0 mm, in which case the center-to-center spacing of the adjacent electrodes would be 3.5 mm (one half of the 7 mm spacing of the exemplary center-to-center electrode spacing of the outer or side columns).

Whether to have the most cathodal electrode as the center electrode of the tripole set, or on one end, is a choice of the physician, and may or may not have a significant impact on the effects of electric stimulation. Using the outer electrodes as anodes, however, may avoid nerve root stimulation.

Tables A, B and C (FIGS. 18-20) include cross references to one or more of FIGS. 7-17, and may be referred to for further illustration of the examples outlined with respect to FIGS. 7-17. Table A (FIG. 18) illustrates various exemplary electrode programs for voltage controlled stimulation; Table B (FIG. 19) illustrates various exemplary electrode programs for voltage controlled stimulation in which cathodal voltage is less than the shield/housing voltage of the neurostimulator 22; and Table C (FIG. 20) illustrates various exemplary electrode programs for current controlled stimulation.

As illustrated in FIGS. 7-9, the two indicated alternative center electrodes (which may be used, e.g., as cathodes) may be slightly offset longitudinally from the outer electrodes (which may be used, e.g., as anodes), thereby increasing the longitudinal component to the electric field generated between the active center electrodes and active outer electrodes. This may help to reduce the amount of electrical energy required for paresthesia, since a longitudinal component of the activating function provides dorsal column stimulation. FIG. 7 includes symbols (+ or −) indicating an exemplary selection of polarity of the active electrodes, and FIGS. 8 and 9 include arrows indicating alternative exemplary directions of electron flow. FIGS. 5-11 illustrate electrode configurations having longitudinal offset such that each outer electrode overlaps laterally across the lead with two center electrodes. FIGS. 5-6 show each electrode of first and second outer columns overlapping laterally with two electrodes of a center third column.

As illustrated in FIGS. 10 and 11, transverse tripole fields may be created by using a pair of central electrodes (e.g., as cathodes). Since epidural electrodes may be at least 2-5 mm away from the spinal cord, if two neighboring electrodes are cathodal, the net effect is substantially like having a single cathode at the center of the pair, or if the neighboring electrodes are anodal, the net effect is substantially like having a single anode at the center of the pair. FIG. 10 includes symbols (+ or −) indicating exemplary polarities of the active electrodes. FIG. 11 includes arrows indicating an exemplary direction of electron flow.

As illustrated in FIGS. 12 and 13, skewed tripole stimulation may be performed (more skewed than FIGS. 7-9). In skewed tripole stimulation, the outer electrodes are not at the same longitudinal location, and one or two cathodes on the middle lead are between the outer two electrodes used. FIG. 12 includes symbols (+ or −) indicating exemplary polarities of the active electrodes. FIG. 13 includes arrows indicating an exemplary direction of electron flow.

FIGS. 14 and 15 illustrate an exemplary programming embodiment in which the electrodes are programmed for field steering. Field steering may be accomplished, for example, by varying the relative (anodal or cathodal) voltage or current of the outer electrodes. FIG. 14 includes symbols (+ or −) indicating exemplary polarity and relative voltages of the active electrodes. FIG. 15 includes arrows indicating an exemplary directions and relative amplitudes of electron flow.

FIGS. 16 and 17 illustrate a wide-field programming exemplary embodiment of TTS with field steering. In this exemplary embodiment, two adjacent electrodes on each outer column and two adjacent electrodes on the central column are shown as active to provide a wider field, and the voltage or current amplitude of the electrodes on the right column are shown as relatively greater than the left column. FIG. 16 illustrates exemplary polarities and relative voltage amplitude of the active electrodes of this embodiment as carried out in a voltage controlled scheme, and FIG. 17 includes arrows indicating exemplary directions and relative amplitudes or electron flow that may be considered as illustrating both current controlled and voltage controlled schemes.

Current-controlled electrical pulses typically have a constant current (I) delivery during the duration of the pulse (pulse width or "PW"). Alternatively, wave-shaping could be used to allow delivery of a changing current during the pulse. Of course, there will be a following pulse of opposite sign at each electrode to keep the net charge delivered zero over time.

Voltage-controlled pulses typically have a constant (V) or decreasing voltage amplitude (V(t)) during the duration of the pulse. Decreasing voltage amplitude over time is common when the pulse comes from a discharging capacitor. Alternatively, wave-shaping techniques could be used to give a V(t) shape that varies during the pulse.

Any system of electrodes that delivers electrical pulses to the body typically include at least one cathode (negative, source of electrons) and at least one anode (positive, source of cations) to have a complete circuit of finite resistance in which currents may flow. When there are only two active electrodes, one is a cathode and one is an anode. Generally, activation of living cells is believed to occur under the cathode (because the negative fields are similar to the negative potential inside a cell, so the trans-membrane potential difference becomes less, until threshold is reached and an action potential begins). Action potentials may also happen at anodes, for example, when a long pulse (typically 1 msec long) ends so the voltage change near the anode becomes depolarizing, or whenever the recharge phase of a pulse for charge balance has a large, rapidly changing amplitude.

When there are three or more active electrodes, and the electrical pulses leaving them are overlapping in time for at least part of their cycle or PW, then electric fields can become complex. A device that delivers current-controlled pulses may have the ability to deliver part of the current, with controlled amplitude, to each chosen anode or cathode. During a pulse, the sum of all outward currents (and charges delivered) would ideally equal the sum of all ingoing currents (and charges brought back). The same is true during the recharge phases, for net charge balance.

Tripoles as discussed in this application are believed to be particularly useful for activating tissue. For example, use of one electrode for a cathodal pulse (either current- or voltage-controlled) and two electrodes that are anodal (also either current- or voltage-controlled), may be used, for example, in spinal cord stimulation, such as used as a therapy for pain. The area in which axons are excited may be limited by the hyper-polarization that occurs near the anodes. As amplitude is increased or decreased, the locus of recruited axons will go farther or nearer to the cathode, but the anodes may tend to shield neural structures beyond the anodes thus tending to prevent their stimulation. If done in a rostral/caudal direction, then it may be comparatively easy to recruit dorsal column fibers. If done in a medial/lateral direction, then it may be comparatively easy to recruit dorsal root fibers.

Since electrodes for spinal cord stimulation tend to be several millimeters away from spinal cord axons, with intervening low impedance cerebrospinal fluid, effects from various electrode combinations and polarities might be sufficiently attenuated that switching electrodes in or out of circuits might not have major effects. For cases where electrodes are very near axons (peripheral nerve stimulation, deep brain stimulation), it may be more important that bringing electrodes into or out of circuits should be done with control of each electrode's impedance, for example, with a series controllable resistor.

FIGS. 27-47 illustrate an exemplary embodiment of an electrode array on a paddle lead in which alternate center electrodes C1, C3 and C5 of the paddle 144 are aligned with opposite side electrodes L0 and R0, L1 and R1 and L2 and R2 respectively. The center-to-center spacing of the electrodes C0, C1, etc. of the central column may be approximately ½ of the center-to-center spacing of the electrodes R0, R1, etc., or L0, L1, etc., of the side or outer columns.

Figure 30:
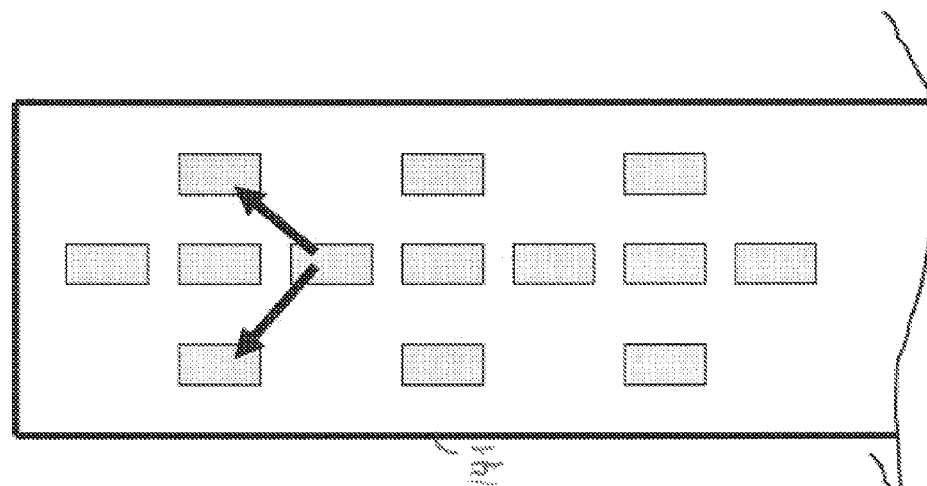
Figure 29:
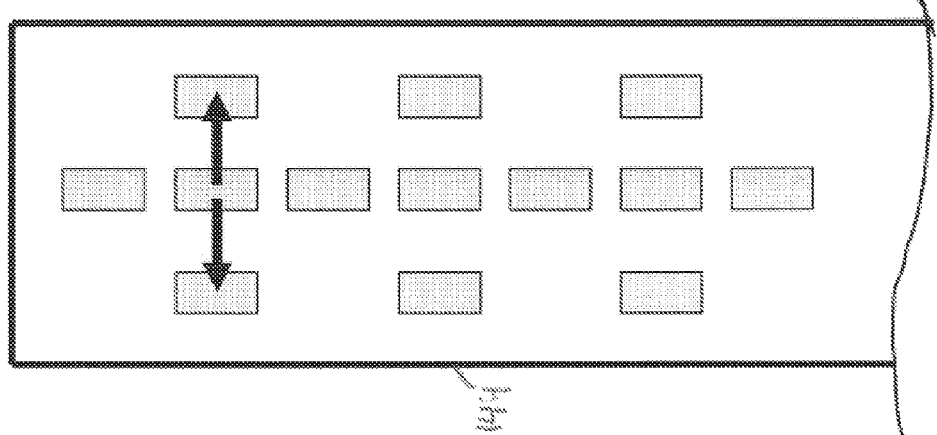
Figure 28:
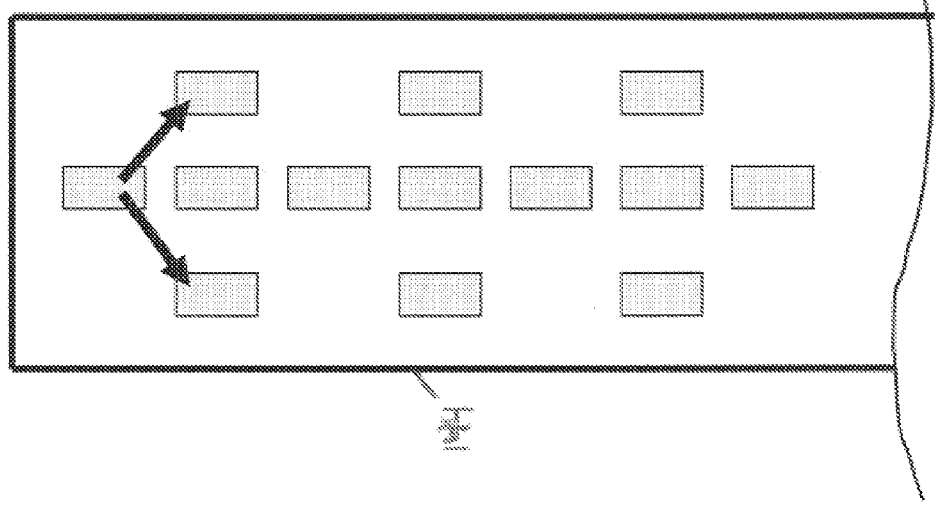

FIGS. 28 and 30 illustrate slightly skewed electrode stimulation configurations in which opposite side electrodes may be anodes and a center electrode that is in the next or adjacent longitudinal position is used as a cathode as opposed to the configuration of FIG. 29 in which the aligned center electrode is used as a cathode. The first three lines of tables D, E and F (FIGS. 48-50) show exemplary voltage or current amplitudes that may be employed in a stimulation program to accomplish the stimulation pattern illustrated in FIGS. 28-30.

FIGS. 31 and 32 illustrate another slightly skewed stimulation pattern in which two opposite side electrodes are anodes and the aligned center electrode, and a center electrode that is in the next or adjacent longitudinal position, are used as cathodes. Exemplary voltage or current amplitudes that may be employed to accomplish these stimulation patterns are illustrated in FIGS. 48-50. It may be appreciated that the electrical field produced by the examples of FIGS. 31 and 32 are less skewed and less focused than provided by the examples of FIGS. 28 and 30.

FIG. 33 illustrates a non-skewed stimulation configuration in which two opposite side electrodes are anodes and the aligned center electrode, and the two center electrodes that are in the next or adjacent longitudinal position on opposite sides of the aligned center electrode, are used as cathodes. Exemplary voltage or current amplitudes that may be employed to accomplish this stimulation pattern are illustrated in FIGS. 48-50. It may be appreciated that the electric field produced by the example of FIG. 33 may both contain a longitudinal component and be non-skewed, while providing less focus than the example of FIG. 29.

Figure 37:
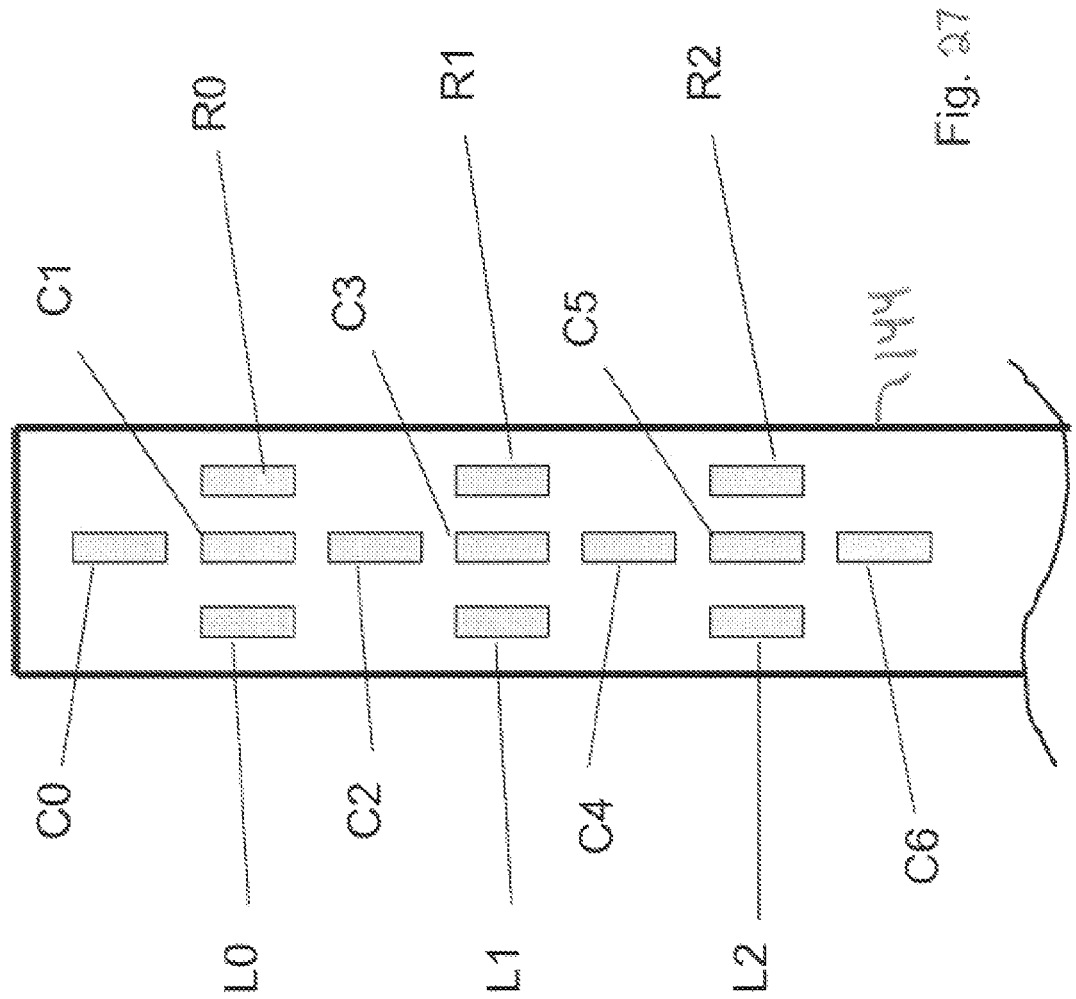
Figure 36:
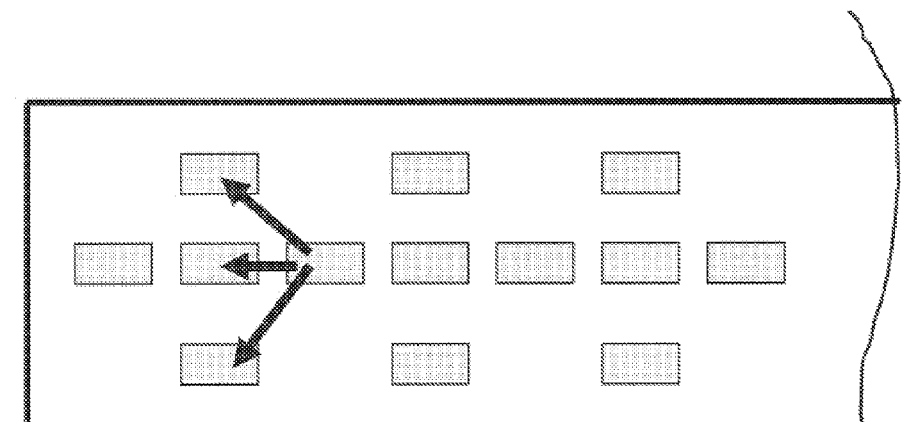
Figure 35:
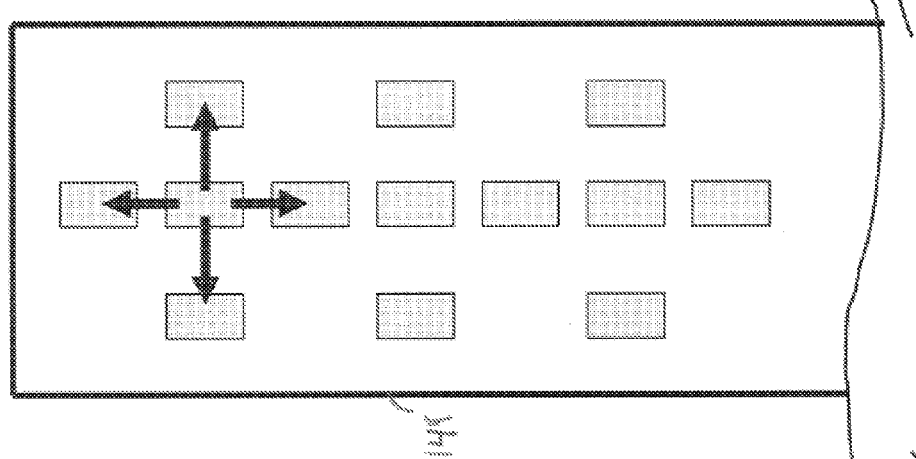
Figure 34:
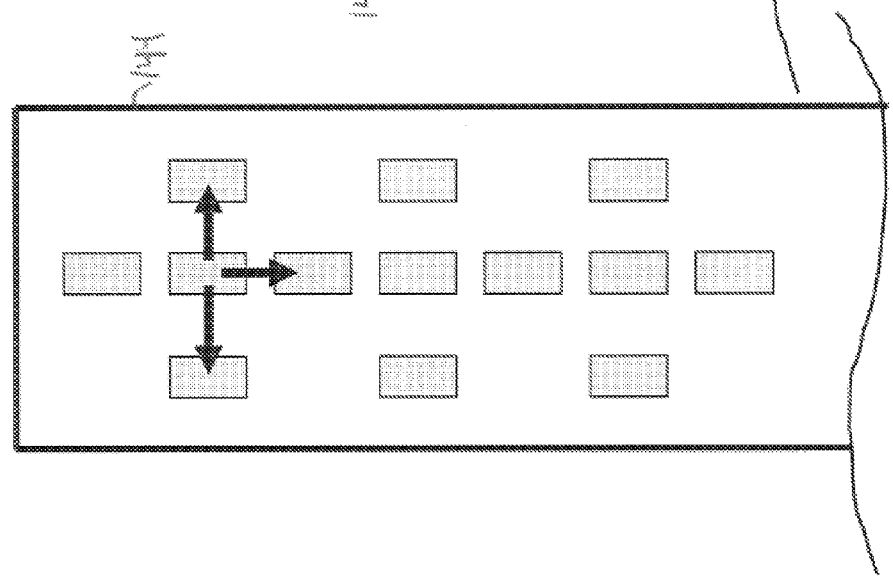
Figure 35:
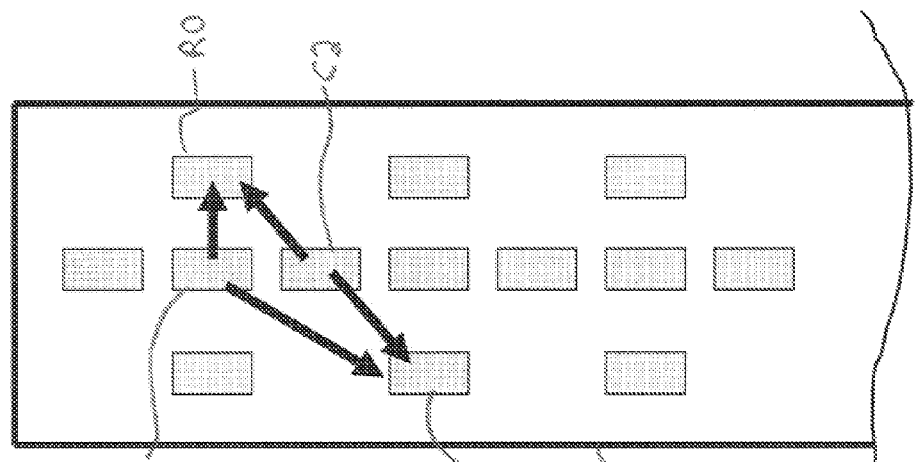
Figure 36:
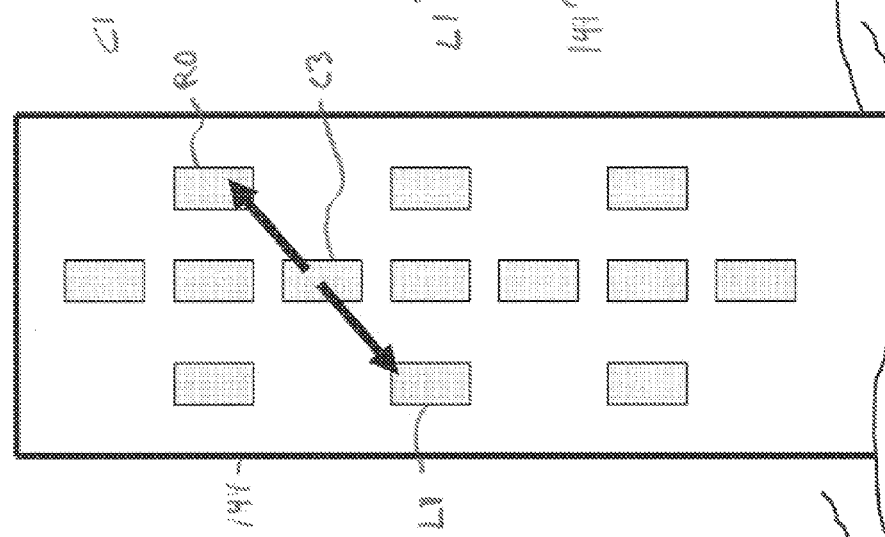
Figure 37:
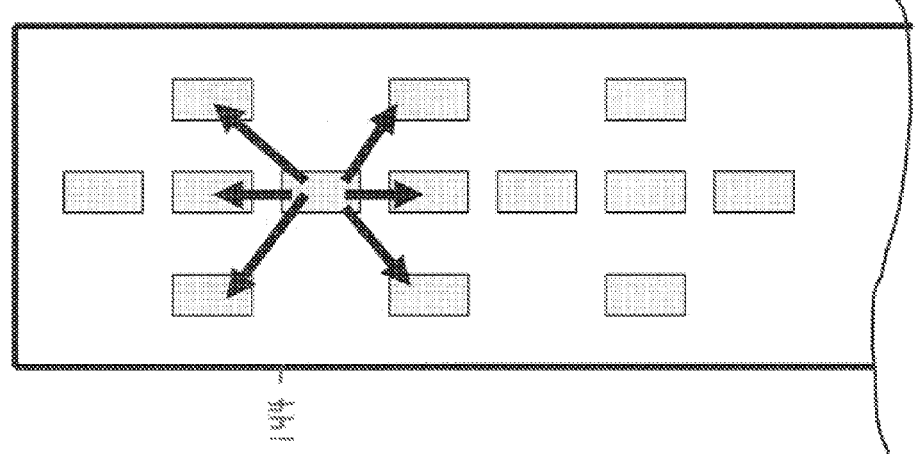

FIG. 34 illustrates a stimulation configuration in which two opposite side electrodes, and a center electrode that is in the next or adjacent longitudinal position, are anodes, and the aligned center electrode is used as a cathode. This allows, among other things, the use of a single center cathode with some degree of skewing or longitudinal component of stimulation provided by the center anode. FIG. 35 is similar in some respects to the pattern illustrated in FIG. 34 except that two center electrodes on opposite sides of the active center electrode (cathode) are programmed as anodes. FIG. 36 is also similar in some respects to the pattern illustrated in FIG. 34 except that the cathode is programmed in the non-aligned or adjacent center electrode and the anode is programmed in the aligned center electrode. FIG. 37 illustrates a stimulation configuration in which two opposite side electrodes, and the two opposite center electrodes that are in the next or adjacent longitudinal position, are anodes, and the aligned center electrode is used as a cathode. Exemplary voltage or current amplitudes that may be employed to accomplish these stimulation patterns are illustrated in FIGS. 48-50.

Figure 41:
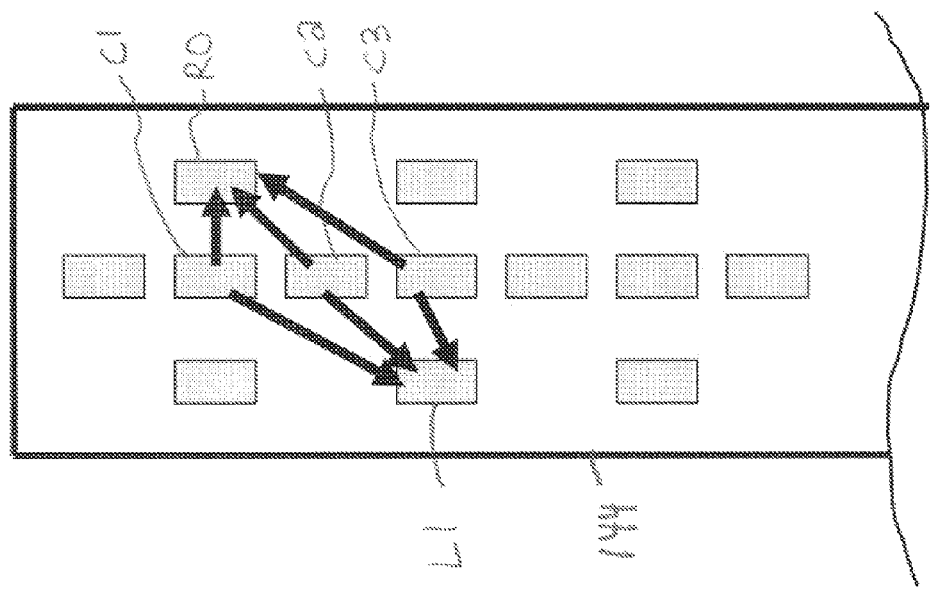
Figure 40:
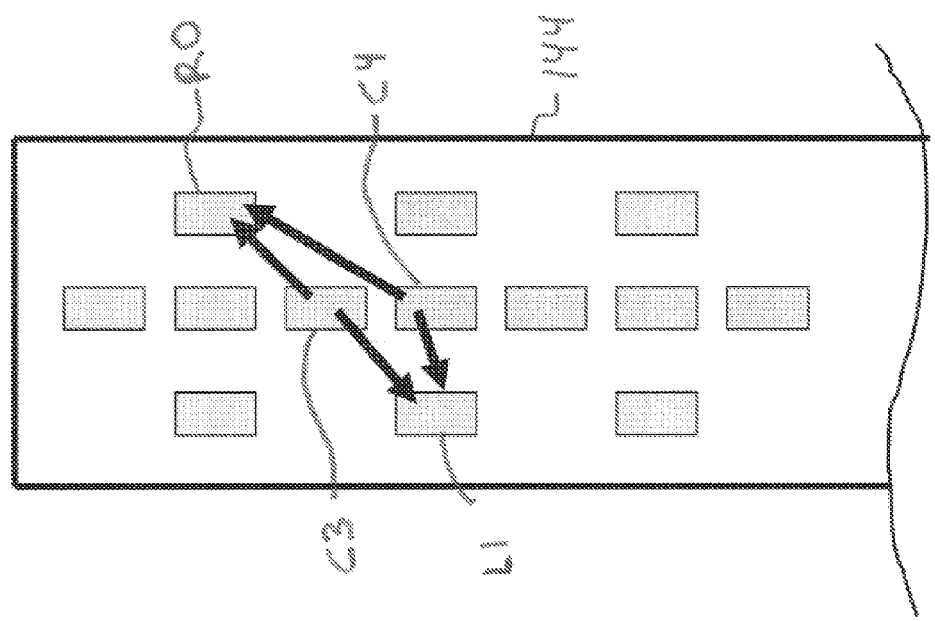

FIG. 38 illustrates a skewed stimulation configuration in which a diagonal array of active stimulation electrodes are employed in an anode/cathode/anode configuration. Side electrodes R0 and L1 are active along with center electrode C3 providing in one example a linear diagonal tripolar array transverse but at an angle to the spinal cord. FIGS. 39 and 40 illustrates a skewed stimulation configuration in which an additional center electrode is added as a cathode either in alignment with the first side electrode, e.g., R0 in FIG. 39, or in alignment with the second side electrode, e.g., L1 in FIG. 40. FIG. 41 illustrates a skewed stimulation configuration in which two additional center electrodes are added as a cathodes (relative to FIG. 38), one (e.g., C1) in alignment with a first side electrode (e.g., R0) and one (e.g., C3) in alignment with a second side electrode (e.g., L1). Exemplary voltage or current amplitudes that may be employed to accomplish these stimulation patterns are illustrated in FIGS. 48-50.

FIGS. 42-47 illustrate various stimulation configurations in which the electrodes are programmed to "steer" the electric field. In this regard, U.S. Pat. No. 5,501,703 is incorporated herein by reference. FIG. 42 illustrates programming the right outer electrode R0 at a higher voltage or current magnitude than the left outer electrode L0.

FIG. 43 illustrates a configuration in which an adjacent center electrode as added to the active array as an additional anode at an exemplary voltage or current magnitude similar to the left outer electrode L0. FIG. 44 is similar to FIG. 43 except that the magnitude of the left outer electrode L0 is increased generally to match or balance the right outer electrode R0. FIG. 45 is similar to FIG. 44 except that an additional adjacent center electrode is added as an anode on the opposite side of the aligned center cathode, with the new center anode generally matching the magnitude of the other center anode. FIGS. 46 and 47 illustrate an additional center cathode on either side of the aligned center cathode to that illustrated in FIG. 42. Exemplary voltage or current amplitudes that may be employed to accomplish these stimulation patterns are illustrated in FIGS. 48-50.

It will be appreciated that the shape and orientation of the elongate direction of the exemplary electrode array of FIGS. 27-47 may be varied as suggested with the other embodiments including without limitation the embodiments illustrated in FIGS. 21-26.

Figure 51:
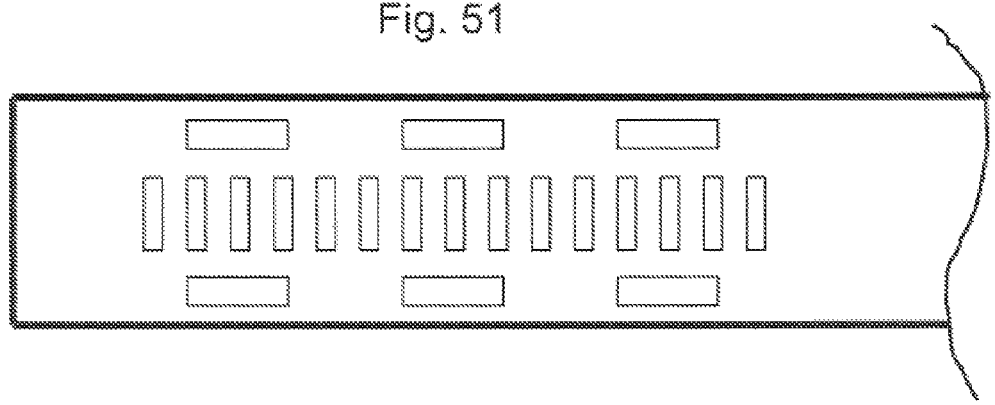
FIGS. 51-53 illustrate additional exemplary embodiments of paddle style leads.
Figure 52:
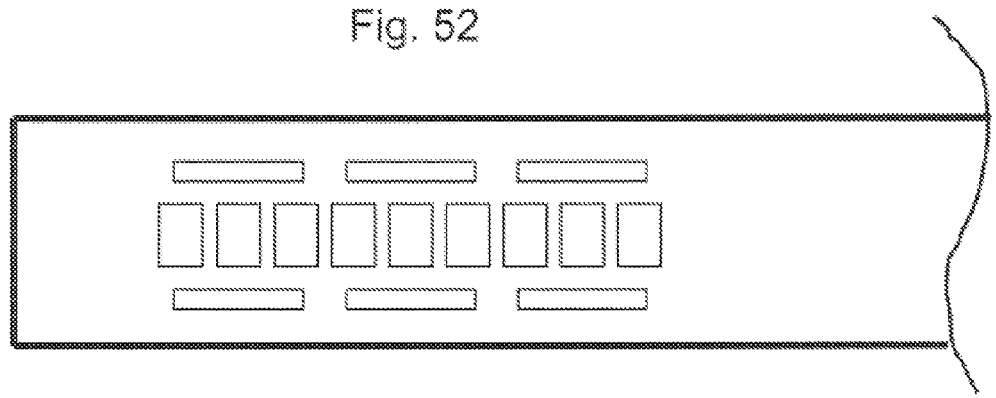
Figure 53:
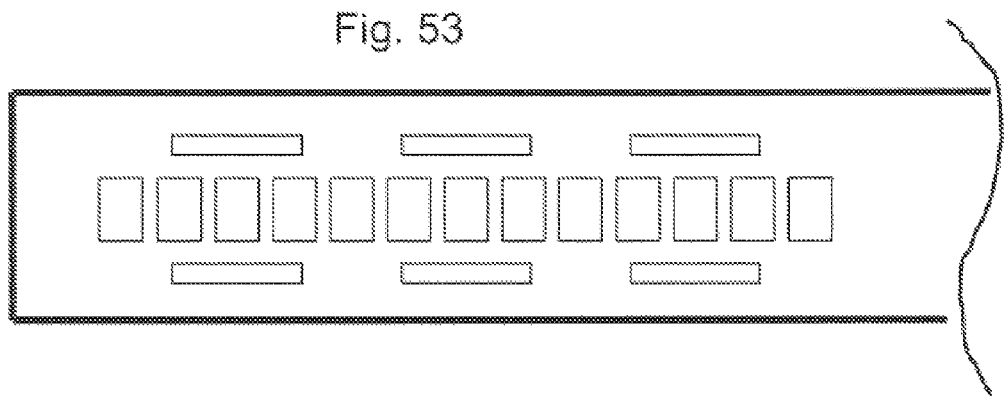

FIGS. 51-53 illustrate additional exemplary embodiments in which there is a five-to-one ratio between center and either side outer electrodes in FIG. 51, a three-to-one ratio between center and either side outer electrodes in FIG. 52, and approximately a four-to-one ratio between center and either side outer electrodes in FIG. 53 (i.e. a four-to-one ratio plus one additional center electrode). It is also contemplated that ratios higher than five-to-one could be employed. The embodiments of these figures may be programmed in a similar fashion to that described with the other embodiments.

It will be appreciated that the embodiments of FIGS. 5-17 have a two-to-one ratio of center column electrodes relative to either side column electrodes, and the embodiments of FIGS. 27-47 have approximately a two-to-one ratio of center column electrodes relative to either side column electrodes (i.e. two-to-one ratio plus one additional center column electrode.

An orientation marker (not shown) may be employed for determining orientation of the lead, with the orientation marking including fluoroscopically viewable material. The orientation marking is displaced from the longitudinal center line of the paddle or is arranged (or dispersed) in a asymmetric manner with respect to the width of the paddle. An exemplary orientation marker is disclosed in co-assigned U.S. Patent Application Publication No. 20040260310 (Harris et al), which is incorporated herein by reference.

Thus, exemplary embodiments of the transverse tripole neurostimulation lead, system, and method are disclosed. The disclosed embodiments are presented for purposes of illustration and not limitation. One skilled in the art will appreciate that the invention may be practiced with embodiments other than those disclosed.

What is claimed is:

1. An implantable electrode array adapted for epidural implantation for electrically stimulating the spinal cord, the electrode array comprising first, second and third longitudinally extending columns with each column including a plurality of stimulation electrodes spaced apart and the first and second columns being laterally spaced apart from the third column along opposite sides of the third column, the stimulation electrodes of the first and second columns having substantially similar center-to-center spacing of adjacent electrodes, and the stimulation electrodes of the third column having a center-to-center spacing of adjacent electrodes that is no greater than approximately one half of the center-to-center spacing of adjacent electrodes of the first and second columns, wherein the plurality of stimulation electrodes for the third column includes at least double the number of electrodes for either the first or second columns.

2. The implantable electrode array according to claim 1 in which the plurality of stimulation electrodes for the first and second columns includes the same number of electrodes.

3. The implantable electrode array according to claim 1 in which the stimulation electrodes of the first and second columns have equal longitudinal electrode length and each electrode of the first and second columns overlap laterally with two electrodes of the third column.

4. The implantable electrode array according to claim 1 in which the ratio of the number of stimulation electrodes of the third column relative to the number of electrodes of either the first or second columns is no more than approximately five.

5. The implantable electrode array according to claim 4 in which the ratio of the number of stimulation electrodes of the third column relative to the number of electrodes of either the first or second columns is an integer value.

6. The implantable electrode array according to claim 1 in which the ratio of the number of stimulation electrodes of the third column relative to the number of electrodes of either the first or second columns is an integer value.

7. The implantable electrode array according to claim 1 in which the plurality of electrodes for each of the first and second columns comprises four electrodes, and the plurality of electrodes for the third column comprises eight electrodes.

8. The implantable electrode array according to claim 1 in which each of the first, second and third columns form a generally parallel array.

9. The implantable electrode array of claim 1 further comprising instructions for use of the implantable electrode array, the instructions specifying use of the implantable electrode array consistent with the following steps:
 implanting the implantable electrode array in the epidural space of a patient; and programming the stimulation electrodes to create a tripole in which at least one electrode is active on each of the first, second and third columns.

10. The implantable electrode array of claim 1 further comprising a label or instructions for use with the implantable electrode array, the label or instructions describing use of the implantable electrode array to form a tripole stimulation pattern.

* * * * *